US009039174B2

(12) United States Patent  
Awasthi et al.

(10) Patent No.: US 9,039,174 B2  
(45) Date of Patent: May 26, 2015

(54) ETHYLENICALLY UNSATURATED POLYMERIZABLE GROUPS COMPRISING POLYCARBOSILOXANE MONOMERS

(71) Applicant: Bausch & Lomb Incorporated, Rochester, NY (US)

(72) Inventors: Alok Kumar Awasthi, Pittsford, NY (US); Jay F. Kunzler, Canandaigua, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 138 days.

(21) Appl. No.: 13/841,145

(22) Filed: Mar. 15, 2013

(65) Prior Publication Data

US 2013/0289294 A1 Oct. 31, 2013

Related U.S. Application Data

(63) Continuation-in-part of application No. 13/781,880, filed on Mar. 1, 2013, now Pat. No. 8,827,447, which is a continuation of application No. 12/832,174, filed on Jul. 8, 2010, now Pat. No. 8,420,711, which is a continuation-in-part of application No. 12/499,854, filed on Jul. 9, 2009, now Pat. No. 7,994,356.

(51) Int. Cl.
C08F 30/08 (2006.01)
C07F 7/08 (2006.01)
C08G 77/50 (2006.01)
C08G 77/20 (2006.01)

(52) U.S. Cl.
CPC .............. C08F 30/08 (2013.01); C07F 7/0852 (2013.01); C07F 7/0854 (2013.01); C08G 77/20 (2013.01); C08G 77/50 (2013.01)

(58) Field of Classification Search
USPC ....... 351/159.33; 523/106; 526/279; 525/100
See application file for complete search history.

(56) References Cited

U.S. PATENT DOCUMENTS

| 3,808,179 | A | | 4/1974 | Gaylord |
| 4,208,506 | A | | 6/1980 | Deichert et al. |
| 4,686,267 | A | | 8/1987 | Ellis et al. |
| 4,910,277 | A | | 3/1990 | Bambury et al. |
| 5,034,461 | A | | 7/1991 | Lai et al. |
| 5,070,215 | A | | 12/1991 | Bambury et al. |
| 5,247,046 | A | * | 9/1993 | Takago et al. .................... 528/15 |
| 5,321,108 | A | | 6/1994 | Kunzler et al. |
| 5,342,913 | A | * | 8/1994 | Takago et al. .................... 528/15 |
| 5,358,995 | A | | 10/1994 | Lai et al. |
| 5,374,662 | A | | 12/1994 | Lai et al. |
| 5,386,049 | A | | 1/1995 | Kishita et al. |
| 5,387,632 | A | | 2/1995 | Lai et al. |
| 5,387,662 | A | | 2/1995 | Kunzler et al. |
| 5,420,324 | A | | 5/1995 | Lai et al. |
| 5,442,083 | A | | 8/1995 | Kobayashi |
| 5,451,651 | A | | 9/1995 | Lai |
| 5,484,868 | A | | 1/1996 | Kobayashi |
| 5,496,871 | A | | 3/1996 | Lai et al. |
| 5,504,175 | A | | 4/1996 | Kobayashi |
| 5,531,929 | A | | 7/1996 | Kobayashi |
| 5,539,016 | A | | 7/1996 | Kunzler et al. |
| 5,578,381 | A | | 11/1996 | Hamada et al. |
| 5,594,085 | A | | 1/1997 | Lai |
| 5,610,252 | A | | 3/1997 | Bambury et al. |
| 5,639,908 | A | | 6/1997 | Lai |
| 5,648,515 | A | | 7/1997 | Lai |
| 5,714,557 | A | * | 2/1998 | Kunzler et al. ............... 526/279 |
| 5,831,110 | A | | 11/1998 | Isoda et al. |
| 5,981,675 | A | * | 11/1999 | Valint et al. .................. 526/279 |
| 5,998,498 | A | | 12/1999 | Vanderlaan et al. |
| 6,080,829 | A | | 6/2000 | Tapsak et al. |
| 6,367,929 | B1 | | 4/2002 | Maiden et al. |
| 6,458,461 | B1 | | 10/2002 | Blair et al. |
| 6,492,480 | B1 | | 12/2002 | Nagashima et al. |
| 6,524,716 | B2 | | 2/2003 | Visel et al. |
| 6,534,587 | B1 | | 3/2003 | Tapsak et al. |
| 6,921,802 | B2 | | 7/2005 | Kunzler et al. |
| 6,943,203 | B2 | | 9/2005 | Vanderlaan et al. |
| 7,763,682 | B2 | * | 7/2010 | Lowery et al. .............. 525/330.3 |
| 7,915,323 | B2 | * | 3/2011 | Awasthi et al. ............... 523/106 |
| 2005/0054802 | A1 | * | 3/2005 | Lai et al. ....................... 528/15 |
| 2006/0106458 | A1 | * | 5/2006 | Jason et al. .................. 623/6.11 |

(Continued)

FOREIGN PATENT DOCUMENTS

| WO | WO97/20851 | 6/1997 |
| WO | WO2008/092048 | 7/2008 |
| WO | WO2009/009527 | 1/2009 |
| WO | 2012/128751 A1 | 9/2012 |
| WO | 2012/128752 A1 | 9/2012 |

OTHER PUBLICATIONS

Lai, Yu-Chin. "The Role of Bulky Polysiloxanylalkyl Methacrylates in Oxygen-Permeable Hydrogel Materials" in J. Appl. Poly. Sci., vol. 56, pp. 317-324 (1995).

Lai, Yu-Chin. "The Role of Bulky Polysiloxanylakyl Methacrylates in Polyurethane-Polysiloxane Hydrogels" in J. App. Poly. Sol., vol. 60, pp. 1193-1199 (1996).

Benjamin, William J. et al. "The Oxygen Permeability of Reference Materials" in Optom. Vis. Sci., 74 (12s): 95 (1997).

(Continued)

Primary Examiner — Satya Sastri  
(74) Attorney, Agent, or Firm — Toan P. Vo

(57) ABSTRACT

The present application relates to novel monomers comprising polycarbosiloxane monomers useful in certain specific embodiments in the manufacture of devices. More particularly, the present application relates to certain ethylenically unsaturated free radical polymerizable monomers comprising polycarbosiloxane monomers. Even more particularly, the present application pertains to monomers comprising polycarbosiloxane monomers which further comprise at least two ethylenically unsaturated free radical polymerizable groups.

20 Claims, No Drawings

(56) References Cited

U.S. PATENT DOCUMENTS

| | | |
|---|---|---|
| 2007/0222094 A1* | 9/2007 | Alli et al. .................... 264/1.32 |
| 2009/0168013 A1 | 7/2009 | Kunzler et al. |
| 2010/0118261 A1* | 5/2010 | McGee et al. ............ 351/160 R |
| 2011/0009519 A1 | 1/2011 | Awasthi et al. |
| 2011/0009587 A1 | 1/2011 | Awasthi et al. |
| 2011/0009658 A1 | 1/2011 | Awasthi et al. |

OTHER PUBLICATIONS

Lohmeijer, Bas G.G. et al. "Organocatalytic Living Ring-Opening Polymerization of Cyclic Carbosiloxanes" in Organic Letters, vol. 8, No. 21, pp. 4683-4686 (2006).

Lu, Ping et al. "Reaction of Dimethyldichlorosilane, Phenylmethyldichlorosilane, or Diphenyldichlorosilane with Dimethyl Sulfoxide" in Organometallics, 1996, 15, pp. 4649-4652.

Piccoli, William et al. "Highly Strained Cyclic-Paraffin Siloxanes" in Organic and Biological Chemistry, Apr. 20, 1960, vol. 82, pp. 1883-1885.

Ziatdinov, Vadim et al. Anionic Ring-Opening Polymerization of Trimethylsiloxy-Substituted 1-Oxa-2,5-disilacyclopentanes . . . : in Macromolecules, 2002, vol. 35, pp. 2892-2897.

U.S. Appl. No. 12/499,853, filed Jul. 9, 2009, Awasthi et al.

U.S. Appl. No. 12/499,854, filed Jul. 9, 2009, Awasthi et al.

International Search Report (PCT/ISA/210) and Written Opinion (PCT/ISA/237) mailed on Mar. 30, 2011.

International Search Report and Written Opinion of the International Searching Authority in corresponding International Application No. PCT/US2014/028112, mailed Jun. 4, 2014 (10 pages).

* cited by examiner

ETHYLENICALLY UNSATURATED POLYMERIZABLE GROUPS COMPRISING POLYCARBOSILOXANE MONOMERS

PRIORITY CLAIMS TO PRIOR APPLICATIONS

This patent application is a continuation in part of U.S. patent application Ser. No. 13/781,880 filed on Mar. 1, 2013; which is a continuation of U.S. patent application Ser. No. 12/832,174 filed on Jul. 8, 2010; which is a continuation in part of U.S. patent application Ser. No. 12/499,854 filed on Jul. 9, 2009, now issued U.S. Pat. No. 7,994,356, the contents of each of which are incorporated by reference herein.

FIELD

The present application relates to novel monomers comprising polycarbosiloxane units useful in certain specific embodiments in the manufacture of biocompatible medical devices. More particularly, the present application relates to certain ethylenically unsaturated free radical polymerizable monomers comprising polycarbosiloxane units. Even more particularly, the present application pertains to monomers comprising polycarbosiloxane units which further comprise at least two ethylenically unsaturated free radical polymerizable groups capable of polymerization to form polymeric compositions having desirable physical characteristics useful in the manufacture of ophthalmic devices. When the polycarbosiloxane unit containing monomer further comprises at least two ethylenically unsaturated free radical polymerizable groups capable of polymerization to form polymeric compositions has the structure of Formulae IIb, L is not a bond and V is not a monovalent ethylenic moiety.

The desirable characteristics of the novel monomers comprising polycarbosiloxane units of the present application would include such characteristics as low modulus of elasticity despite increased cross link density, improved lubricity and improved hydrolytic stability. Other advantages may present themselves when monomers comprising polycarbosiloxane units are used in applications outside of the biomedical device field of art.

BACKGROUND AND SUMMARY

Various articles, including biomedical devices, are formed of organosilicon-comprising materials. One class of organosilicon-comprising materials useful for biomedical devices, such as soft contact lenses, is hydrogel materials comprising silicones. A hydrogel is a hydrated, cross-linked polymeric system that contains water in an equilibrium state. Hydrogel contact lenses offer relatively high oxygen permeability as well as desirable biocompatibility and comfort. The inclusion of a silicone, i.e., a siloxy unit containing material, in a hydrogel formulation is the presence of siloxy units in the polymerized material of a device generally provides higher oxygen permeability since silicone based materials have higher oxygen permeability than water.

Organosilicon-comprising materials useful for biomedical devices, including contact lenses, are disclosed in the following U.S. patents: U.S. Pat. No. 4,208,506 (Deichert et al.); U.S. Pat. No. 4,686,267 (Ellis et al.); U.S. Pat. No. 5,034,461 (Lai et al.); and U.S. Pat. No. 5,070,215 (Bambury et al.).

U.S. Pat. Nos. 5,358,995 and 5,387,632 describe hydrogels made from various combinations of silicone macromers, TRIS, n-vinyl pyrrolidone (NVP) and DMA. Replacing a substantial portion of the silicone macromer with TRIS reduced the modulus of the resulting hydrogels. Two publications from the same author, "The Role of Bulky Polysiloxyalkyl Methacrylates in Polyurethane-Polysiloxane Hydrogels", *J. Appl. Poly. Sci.*, Vol. 60, 1193-1199 (1996), and "The Role of Bulky Polysiloxyalkyl Methacrylates in Oxygen-Permeable Hydrogel Materials", *J. Appl. Poly. Sci.*, Vol. 56, 317-324 (1995) also describe experimental results indicating that the modulus of hydrogels made from reaction mixtures of silicone-macromers and hydrophilic monomers such as DMA decreases with added TRIS. The addition of methacryloxypropyltris(triethykiloxy)silane (TRIS) reduced the modulus of such hydrogels, but in many examples the modulus is still higher than may be desired.

U.S. Pat. No. 4,208,506 describes monomeric polyparaffinsiloxanes capped with activated unsaturated groups and polymers and copolymers thereof. The monomers of U.S. Pat. No. 4,208,506 are cross-linkers. However, there still remains a need in the art for new monomers to provide silicone hydrogels which are soft enough to make soft contact lenses, which possess additional desirable properties such as high oxygen permeability, suitable water content, and sufficient elasticity, and are comfortable to the contact lens wearer. Prior to the invention as claimed herein, hydrolytically resistant polymeric silicon comprising hydrogel materials have been limited to those comprising at least one siloxane unit, i.e., -[silyl-siloxy]-. Therefore, there is a need for a new type of siloxy comprising unit for producing hydrolytically resistant polymeric silicon comprising materials. That need is addressed by the invention as claimed herein.

BRIEF DESCRIPTION OF THE DRAWINGS

None.

DETAILED DESCRIPTION

Unless clearly stated otherwise all materials used in forming a monomer or monomer mix are listed as weight percent. Also, unless clearly stated otherwise it will be understood that all amounts of materials used to make the monomers and monomer mixes disclosed herein represent the statistical mean of a normal distribution of weight values such as are ordinarily encountered in the laboratory or commercial manufacture of the monomers and monomer mixes disclosed herein. Therefore, unless clearly stated otherwise, all numerical values shall be understood as being modified by the term "about".

As used herein the expressions "polycarbosiloxane monomer" or "EDS" refer to monomers having at least one -[silyl-alkyl-siloxy]- unit or at least one -[silyl-alkenyl-siloxy]- unit. The -[silyl-alkyl-siloxy]- unit or -[silyl-alkenyl-siloxy]- unit may be substituted at any atom capable of having a substituent group and the -[silyl-alkyl siloxy]- unit or -[silyl-alkenyl-siloxy]- unit may be a repeating group. The alkyl portion of the -[silyl-alkyl-siloxy]- unit is a linking group between the silyl and siloxy substituents and is preferably 2-7 carbon atoms in length. These carbon atoms are generally saturated with hydrogen atoms or other monovalent substituent groups but C=C double bonds may also be present in the 2-7 carbon atoms linking the silyl and siloxy substituents thereby providing a -[silyl-alkenyl-siloxy]- unit.

The term "monomer" as used herein refers to varying molecular weight compounds (i.e. typically having number average molecular eights from about 300 to about 100,000) that can be polymerized, and to medium to high molecular weight compounds or polymers, sometimes referred to as macromonomers, (i.e., typically having number average molecular weights greater than 600) comprising functional groups capable of further polymerization. Thus, it is understood that the terms "organosilicon-comprising monomers", "silicone-comprising monomers" and "hydrophilic monomers" include monomers, macromonomers and prepolymers. Prepolymers are partially polymerized monomers or monomers which are capable of further polymerization.

An "organosilicon-comprising monomer" contains at least one siloxy or at least one -[silyl-alkyl-siloxy]- or at least one -[silyl-alkenyl-siloxy]- repeating unit, in a monomer, macromer or prepolymer. In certain embodiments, the total Si and attached O present in the organosilicon-comprising monomer is an amount greater than 5 weight percent. In other embodiments the total Si and attached O present in the organosilicon-comprising monomer is an amount greater than 30 weight percent of the total molecular weight of the organosilicon-comprising monomer. A "silicone-comprising monomer" is one that contains at least one -[siloxy]- repeating unit, in a monomer, macromer or prepoly er.

In a first aspect, the application relates to monomers of formula):

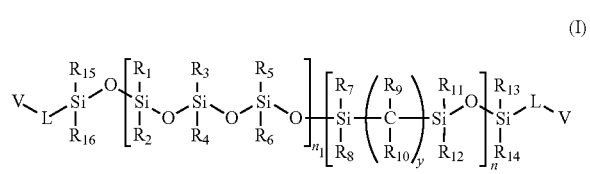

Wherein $R_1$, $R_2$, $R_3$, $R_4$, $R_5$, $R_6$, $R_7$, $R_8$, $R_{11}$, $R_{12}$, $R_{13}$, $R_{14}$, $R_{15}$, and $R_{16}$ are independently a monovalent atom or group including H, alkyl, halo alkyl, heteroalkyl, cyclo alkyl, heterocyclo alkyl, alkenyl, halo alkenyl, or aromatic; as would be understood by one of ordinary skill in the art, $R_9$ and $R_{10}$ may not be present when monomers of formula (I) comprise -[silyl-alkenyl-siloxy]- units and when present in a monomer comprising -[silyl-alky-siloxy]- units are independently a monovalent atom or group including H, alkyl, alkene, alkyne; wherein at least one of $R_9$ or $R_{10}$ is hydrogen; y is 2-7; n is 1-100; $n^1$ is 0-10; L is the same or different and is a divalent linker group or a bond; and V is an ethylenically unsaturated free radical polymerizable monovalent group.

In a second aspect, the application relates to monomers of formula (II):

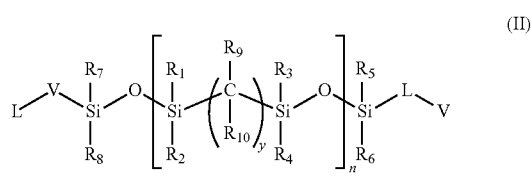

wherein L, V, $R_1$, $R_2$, $R_3$, $R_4$, $R_5$, $R_6$, $R_7$, $R_8$, $R_9$, $R_{10}$, y and n are as defined above. As would be understood by one of ordinary skill in the art, $R_9$ and $R_{10}$ may not be present when monomers of formula (II) comprise -[silyl-alkenyl-siloxy]- units and when present in a monomer comprising a -[silyl-alkenyl-siloxy]- unit are independently a monovalent atom or group including H, alkyl, alkene, alkyne; wherein at least one of $R_9$ or $R_{10}$ is hydrogen.

Additional preferred embodiments of the monomers of the application herein would include monomers of formula (IIb):

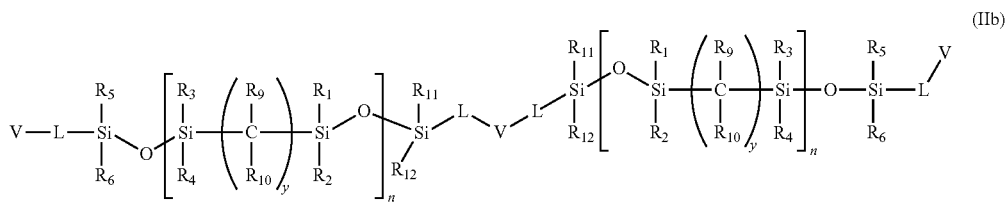

wherein L, V, $R_1$, $R_2$, $R_3$, $R_4$, $R_5$, $R_6 R_9$, $R_{10}$, $R_{11}$, $R_{12}$, y and n are as defined above. As would be understood by one of ordinary skill in the art, $R_9$ and $R_{10}$ may not be present when a monomer of formula (IIb) comprises a -[silyl-alkenyl-siloxy]- unit and when present in a monomer comprising a -[silyl-alkenyl-siloxy]- unit are independently an atom or monovalent group including H, alkyl, alkene, alkyne; wherein at least one of $R_9$ or $R_{10}$ is hydrogen.

Linker groups such as those mentioned above can be a bond or any divalent radical moiety and include substituted or unsubstituted alkyl, alkyl ether, alkenyls, alkenyl ethers, halo alkyls, substituted or unsubstituted siloxanes, and siloxane anions.

Ethylenically unsaturated free radical polymerizable groups are well known to those skilled in the art. Non-limiting examples of ethylenically unsaturated free radical polymerizable groups would include monovalent acrylates, monovalent methacrylates, monovalent vinyl carbonates, monovalent O-vinyl carbamates, monovalent N-vinyl carbamates, monovalent acrylamides and monovalent methacrylamides.

Additional preferred embodiments of the monomers of the application herein would include monomers of the following formulas III and IV:

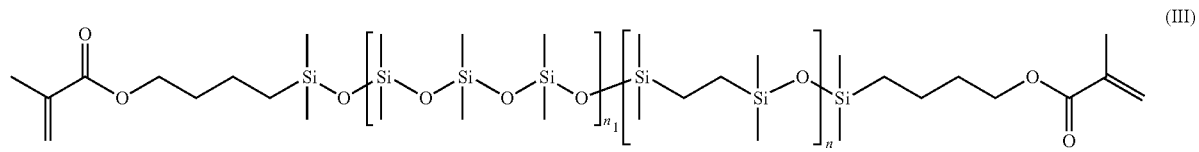

wherein n and $n^1$ are as defined above; and,

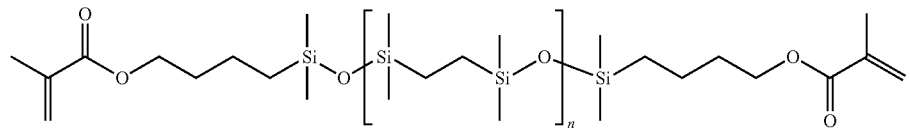

wherein n is 1-100, preferably n is 2-80, more preferably n is 3-20, most preferably n is 5-15.

Additional preferred embodiments of the monomers of the application herein would include monomers of the following formulas: (V)-(VII)

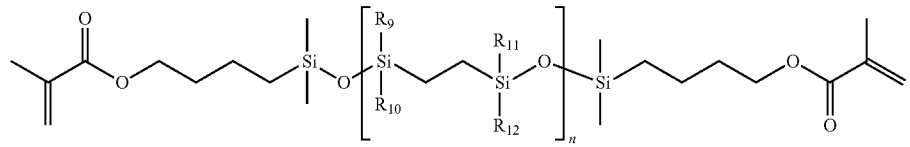

wherein $R_9$, $R_{10}$, $R_{11}$, and $R_{12}$ are as defined above.

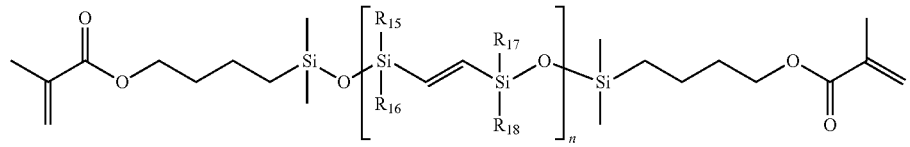

wherein $R_{15}$, $R_{16}$, $R_{17}$ and $R_{18}$ are a monovalent atom or group including hydrogen, or monovalent alkyl, alkene or alkyne groups and at least one of $R_{15}$, $R_{16}$, $R_{17}$ and $R_{18}$ is hydrogen.

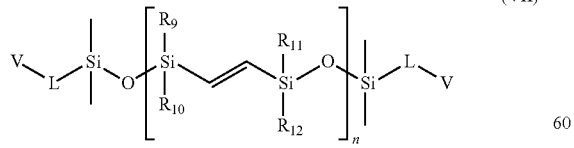

wherein V, L, $R_9$, $R_{10}$, $R_{11}$, and $R_{12}$ are as defined above.

Additional preferred embodiments of the monomers of the application herein would include monomers of the following formulas VIII-XII:

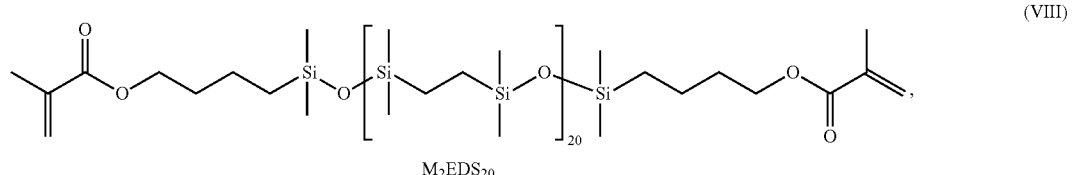
(VIII)
M₂EDS₂₀
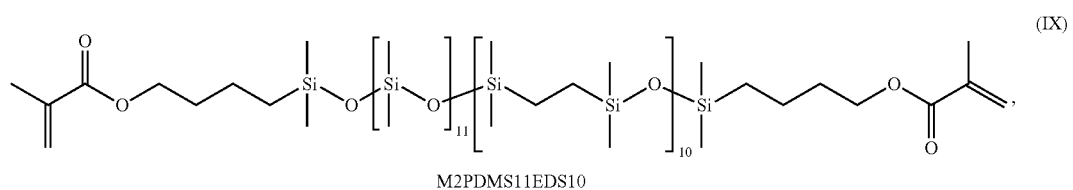
(IX)
M2PDMS11EDS10
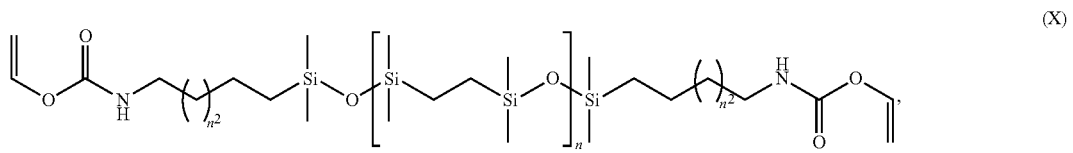
(X)
Wherein n is as defined above and $n^2$ is 0 to 10;
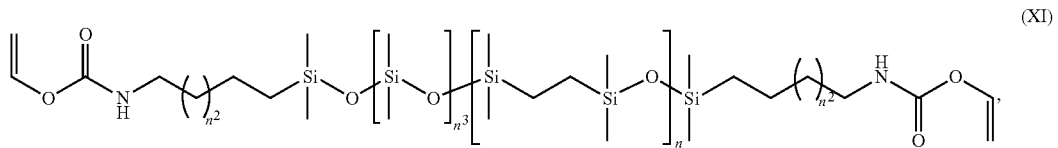
(XI)
wherein n and $n^2$ is as defined above and $n^3$ is 1-10; and
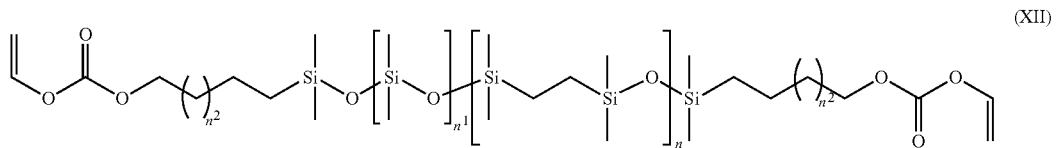
(XII)
Wherein n, $n^1$, and $n^2$ are as defined above.
Additional preferred embodiments of the monomers of the application herein would include monomers of the following formulas XIII-XV:
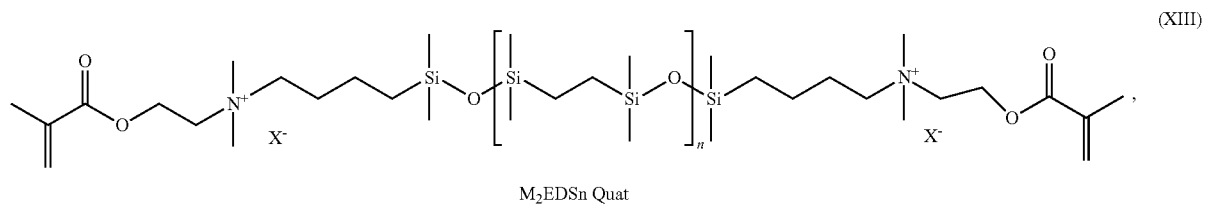
(XIII)
M₂EDSn Quat
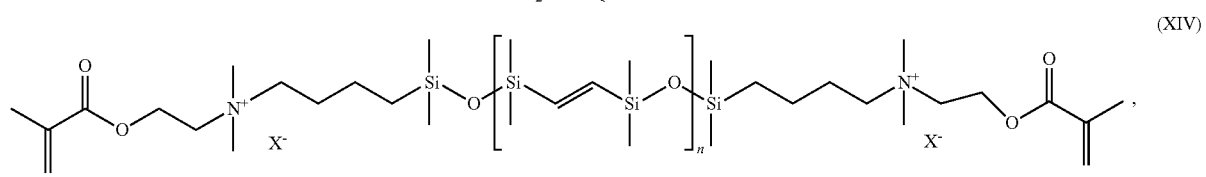
(XIV)

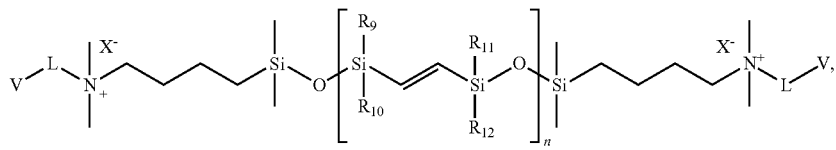
(XV)

wherein n is as defined above; X⁻ is a counter ion to provide an overall neutral charge and V, L, $R_9$, $R_{10}$, $R_{11}$, and $R_{12}$ are as defined above;

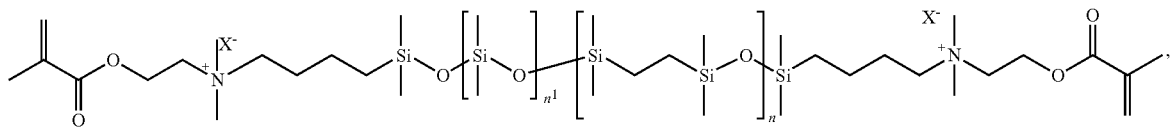
(XVI)

Wherein n and $n^1$ are as defined above and X⁻ is a counter ion to provide an overall neutral charge;

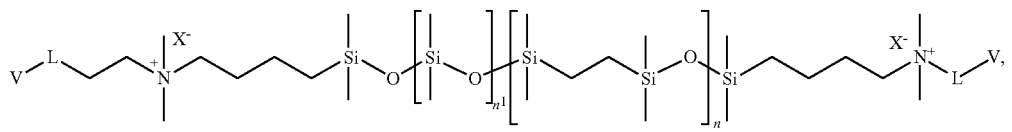
(XVII)

Wherein n, $n^1$, V and L are as defined above and X⁻ is a counter ion to provide an overall neutral charge;

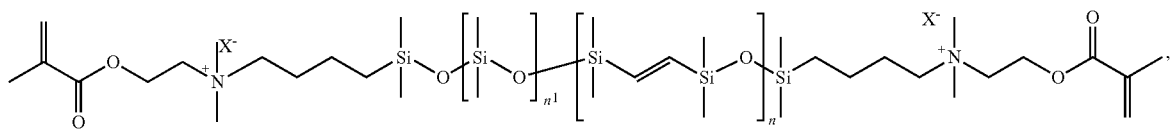
(XVIII)

Wherein n and $n^1$ are as defined above and X⁻ is a counter ion to provide an overall neutral charge; and,

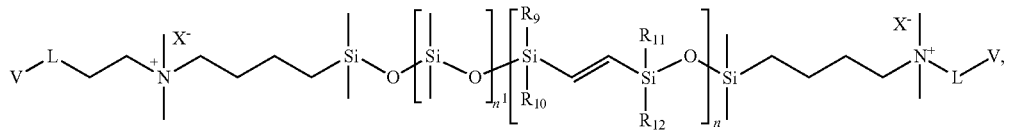
(XIX)

Wherein n, $n^1$, V, L, $R_9$, $R_{10}$, $R_{11}$, and $R_{12}$ are as defined above.

Counter ions capable of providing an overall neutral charge are well known to those of ordinary skill in the art and would include, for example, halide and borate ions.

Additional preferred embodiments of the monomers of the application herein would include monomers of the following formulas XX-XXV:

(XX)
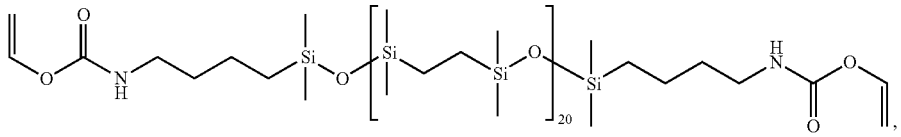
VMa2-EDS20

(XXI)
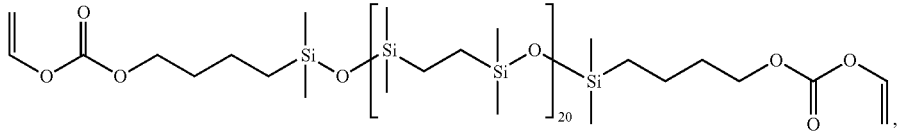
VM2-EDS20

(XXII)
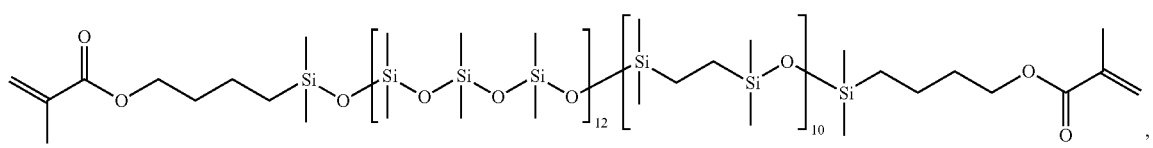
M2-D12-EDS10

(XXIII)
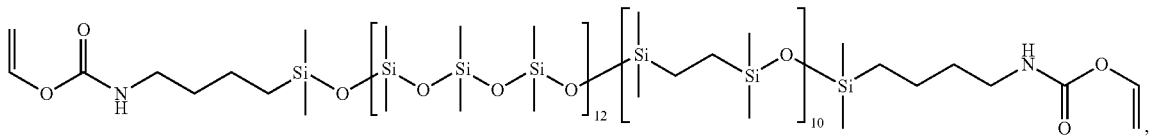
VMa2-D12-EDS10

(XXIV)
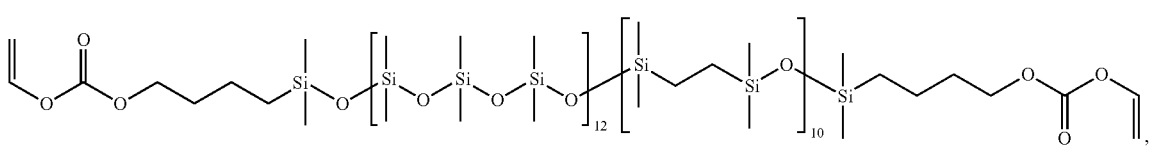
VM2-D12-EDS10

(XXV)
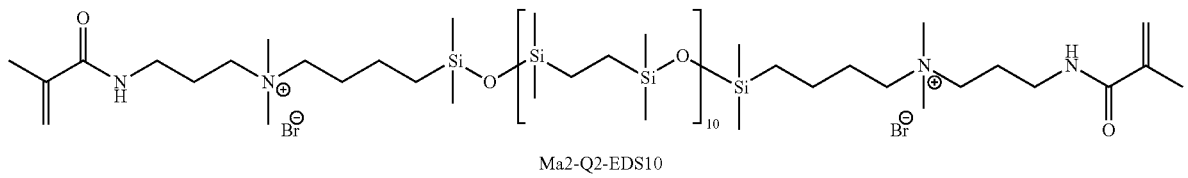
Ma2-Q2-EDS10

Monomers of formula I can be prepared by various synthetic methods, for example:

(XXVI)
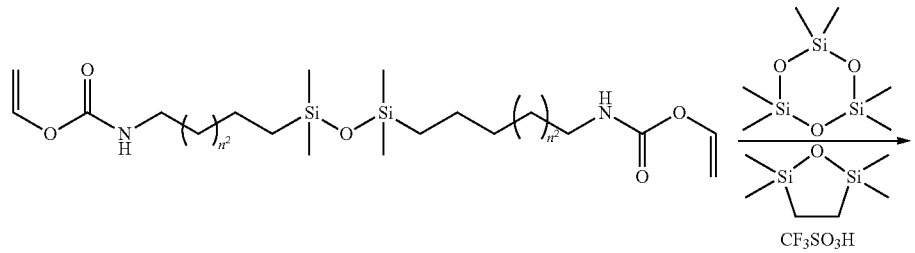

-continued
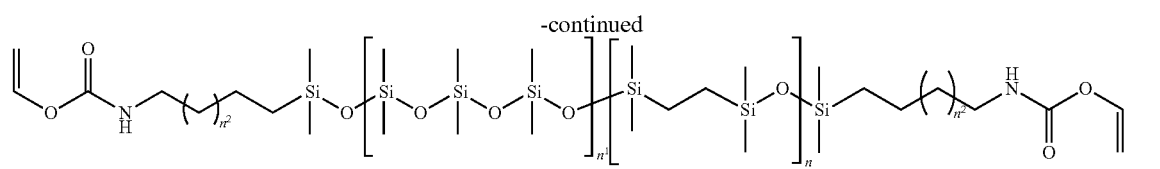
(XXVII)
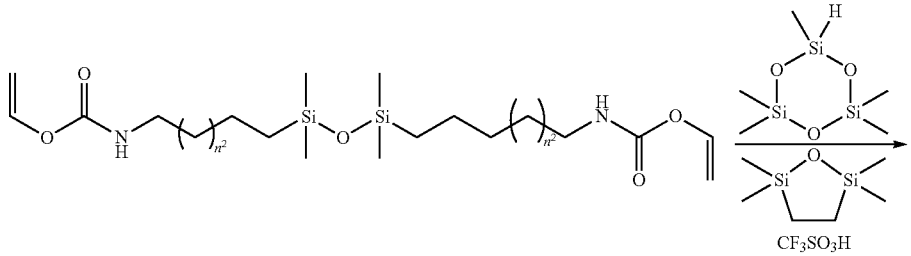
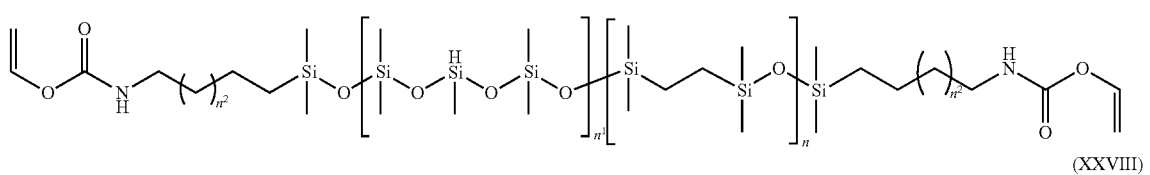
(XXVIII)
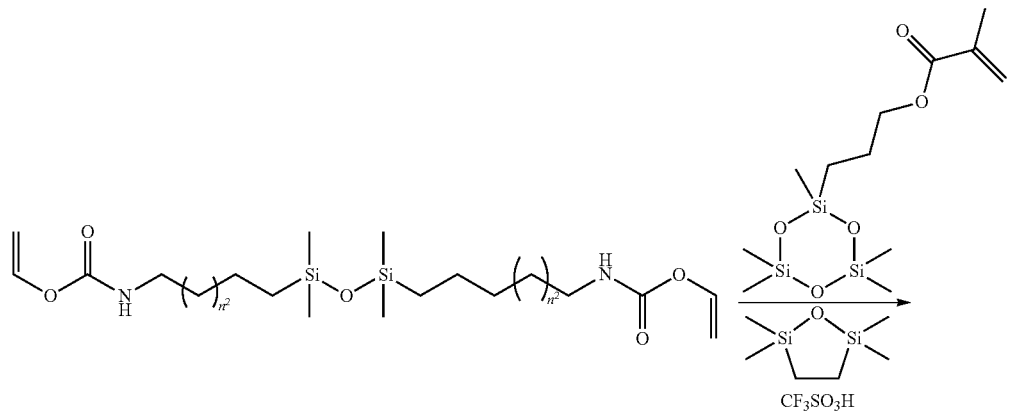
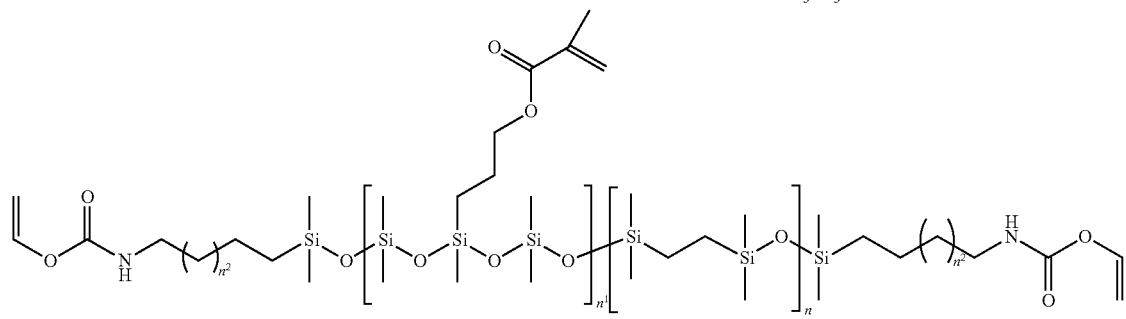
Wherein n, $n^1$ and $n^2$ are as defined above.
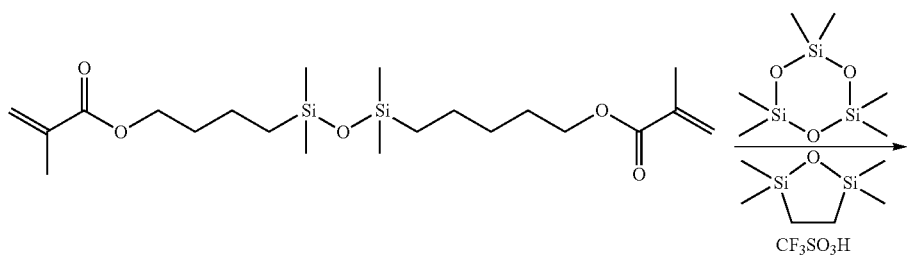

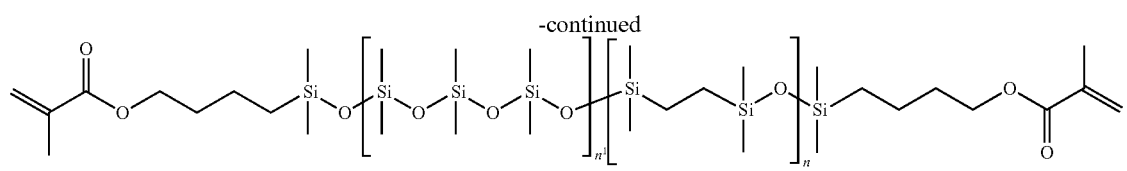
(XXIX)
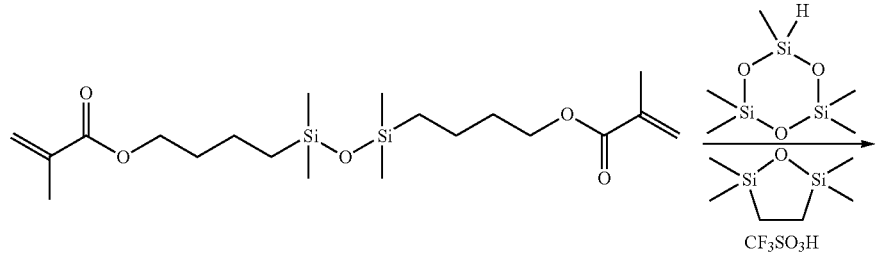
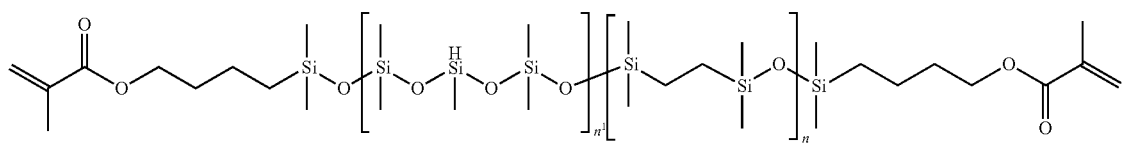
(XXX)
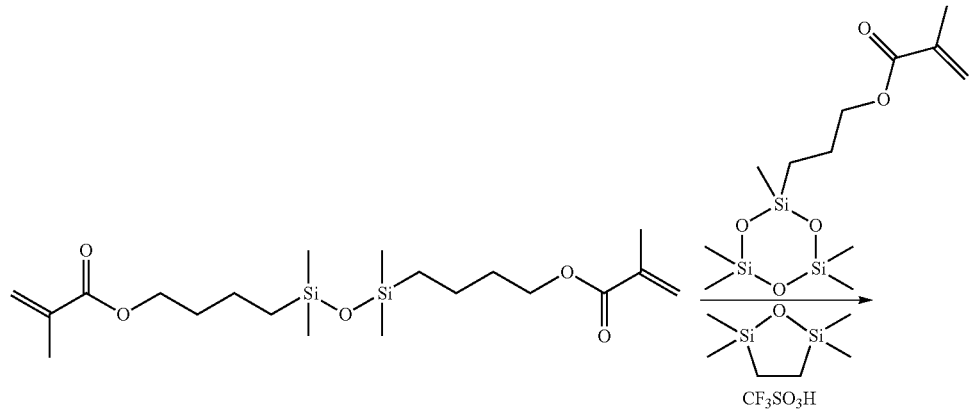
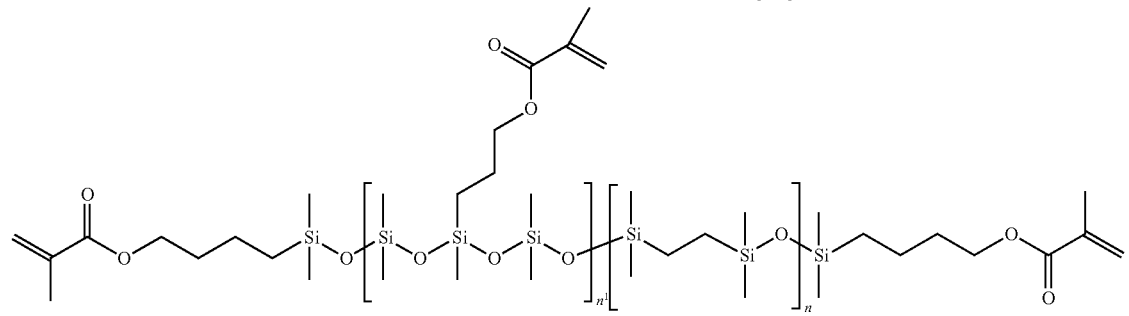
Wherein n, $n^1$ and $n^2$ are as defined above.
Monomers of formula II can be prepared by various synthetic methods, for example:
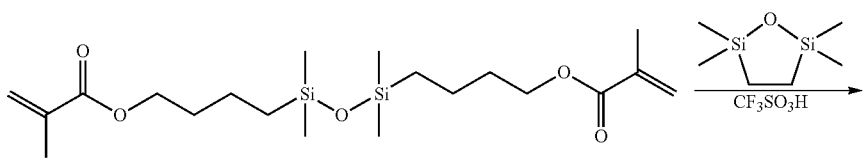

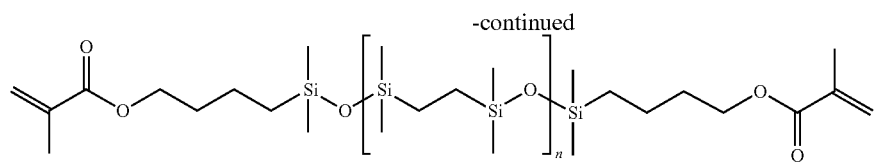
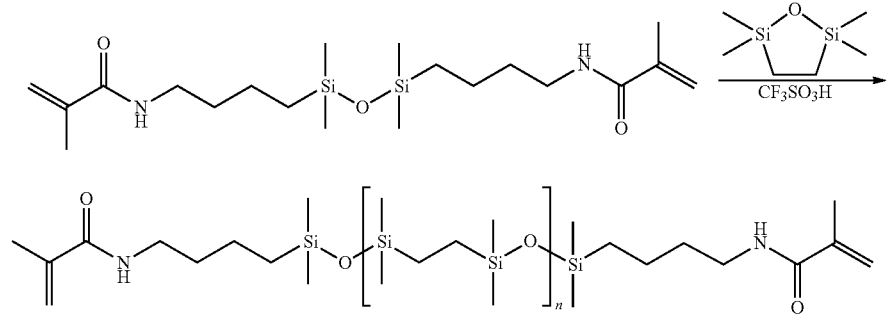
(XXXI)
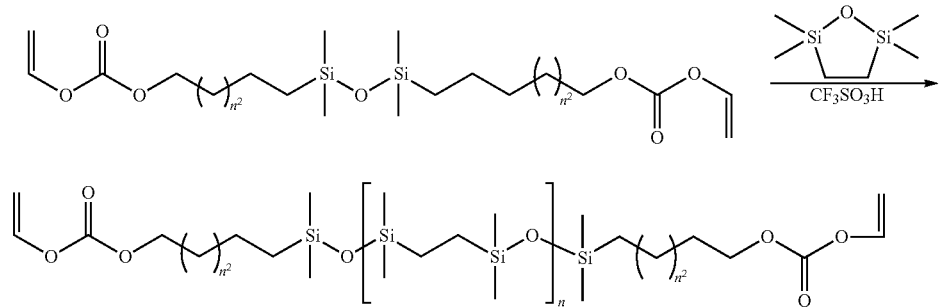
(XXXII)
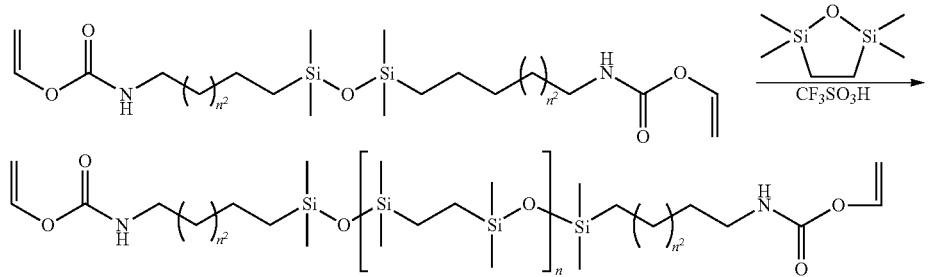
(XXXIII)
Wherein n, $n^1$ and $n^2$ are as defined above.
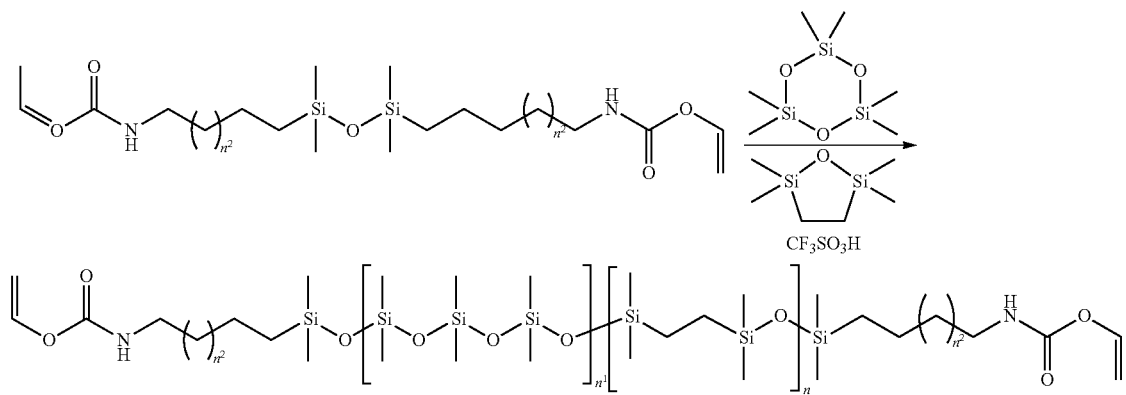

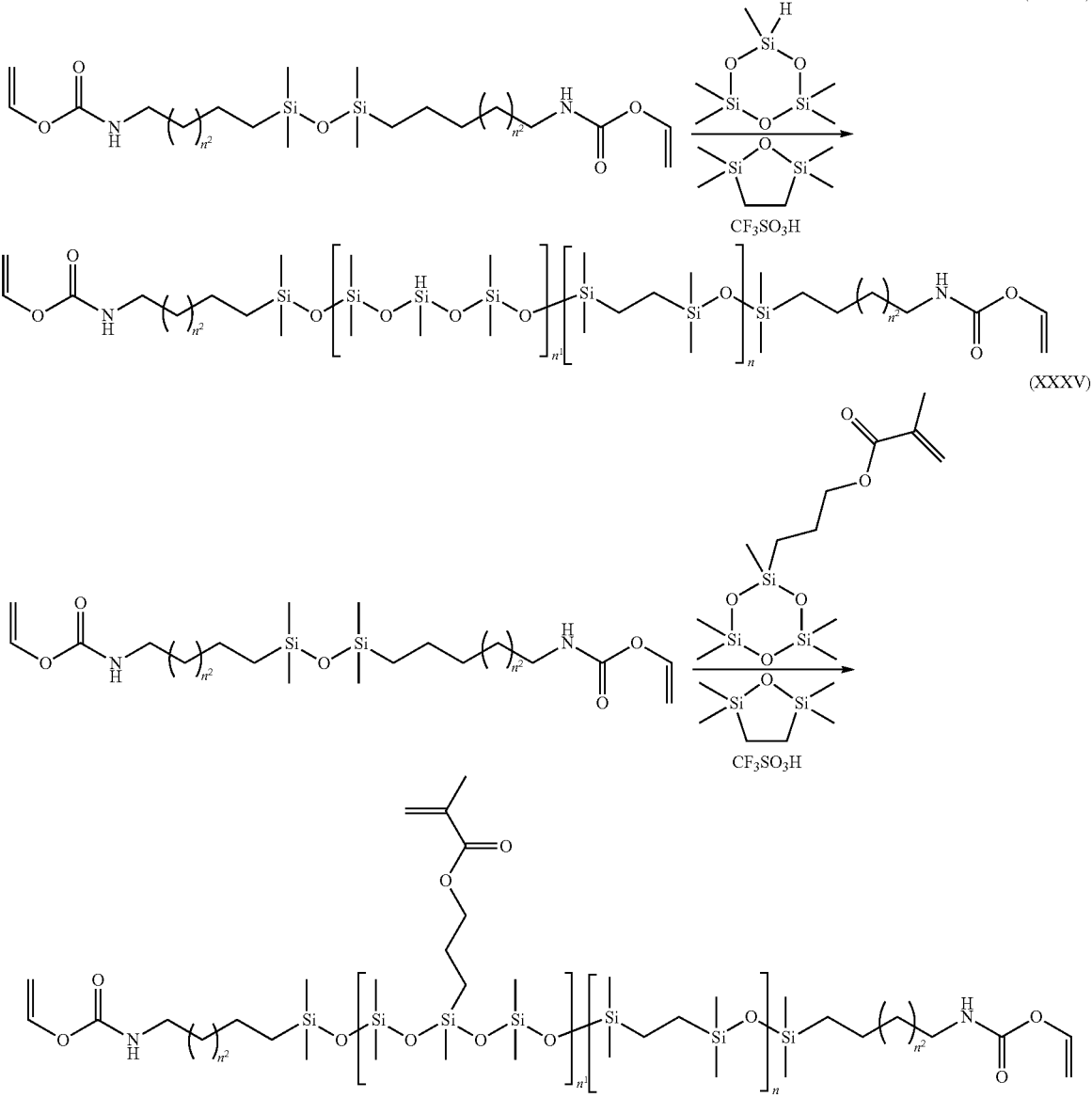

Wherein n, $n^1$ and $n^2$ are as defined above.

In yet another aspect, the application includes any article of manufacture or composition of matter comprising a polycarbosiloxane unit. The article of manufacture or composition of matter comprising a polycarbosiloxane unit may comprise, alone or in any combination, any of the monomers of formulas I-XXXVIII. These articles would include for example any article that silicones have been traditionally used for. For example, Aquarium joints, Automotive, Coatings, Cookware, Defoaming, Dry cleaning, Electronics, Firestops, Lubricants, Medicine, Moldmaking, Ophthalmology, Personal care, Plumbing and building construction, and Toys.

In yet another aspect, the application includes any article or composition of matter comprising, alone or in combination, any articles formed of polymerized article forming monomer mixes comprising, alone or in combination, any of the monomers of formulas I-XXXVIII. According to preferred embodiments, the article is the polymerization product of a mixture comprising at least one of the aforementioned monomers of formulas I-XXXVIII and at least a second free radical copolymerizable monomer. The invention as claimed in this application is useful in certain embodiments for forming a wide variety of articles of manufacture, e.g., either rigid or soft ophthalmic materials for implantation on or in an eye. Especially preferred articles of manufacture are ophthalmic lenses including contact lenses, phakic and aphakic intraocular lenses and corneal implants; although all polymeric materials including, for example, sealants, adhesives, lubricants, medical applications, cookware, and insulation are envisioned as being within the scope of this invention so long as they comprise in some form at least one of the aforementioned monomers of formulas I-XXXVIII, either alone or in any combination. The article of manufacture is selected from the group consisting of biomaterials, adhesives, cosmetics and sealants. Preferred articles of manufacture are optically clear and useful as a contact lens.

The article of manufacture may be made of a polymerized monomer mix as claimed in this application and in further embodiments can provide medical devices such as artificial heart valves, buttons for lathing lenses, films, surgical devices, vessel substitutes, intrauterine devices, membranes, diaphragms, surgical implants, artificial blood vessels, artificial ureters, artificial breast tissue and membranes intended to come into contact with body fluid outside of the body, e.g., membranes for kidney dialysis and heart/lung machines and the like, catheters, mouth guards, denture liners, ophthalmic devices, and especially hydrogel contact lenses.

As set forth above, unless clearly stated otherwise it will be understood that all amounts of materials used to make the monomers and monomer mixes disclosed herein represent the statistical mean of a normal distribution of weight values such as are ordinarily encountered in the laboratory or commercial manufacture of the monomers and monomer mixes disclosed herein. Therefore, unless clearly stated otherwise, all numerical values shall be understood as being modified by the term "about".

Useful concentrations of the ethylenically unsaturated free radical polymerizable group comprising polycarbosiloxane monomers of the invention as claimed in this application herein would include 0.1 to 30 percent by weight of the monomer mix. Other embodiments would have concentrations including 0.1 to 20 percent by weight. Further embodiments would have concentrations including 5 to 15 percent by weight.

Preferred compositions of the monomer mix have both hydrophilic and hydrophobic monomers. Depending upon the specific application, useful articles made with these materials may require additional (other than the subject mono ethylenically unsaturated free radical polymerizable group comprising polycarbosiloxane monomers) hydrophobic, possibly silicone comprising monomers. These additional silicone comprising hydrophobic monomers will be present at between 0.1 to 75.8 percent by weight, in another embodiment between 2 to 20 percent by weight, and in yet a further embodiment between 5 to 13 percent by weight. In certain embodiments amounts of non silicone comprising hydrophobic monomers will be 0 to 60 percent by weight. Examples of non silicone comprising hydrophobic monomers include alkyl acrylates and alkyl methacrylates. A further embodiment might contain silicone comprising hydrogel forming materials.

Depending upon the application, useful articles may also require bulky monomers such as those disclosed in U.S. Pat. No. 6,921,802 which include methacryloxypropyl tris(trimethylsiloxy)silane ("TRIS"), penta ethyldisiloxy methylmethacrylate, tris(trimethylsiloxy)methacryloxy propylsilane, phenyltretramethyl-disloxanylethyl acrylate, methyldi(trimethylsiloxy)methacryloxymethyl silane, 3-[tris(trimethylsiloxy)silyl]propyl vinyl carbamate, 3[tris(trimethylsiloxy)silyl]propyol allyl carbamate, and 3-[tris(trimethylsiloxy)silyl]propyl vinyl carbonate. These bulky monomers, when present in certain embodiments, may be present at 0 to 41.2 percent by weight, 34 to 41 percent by weight or even 25 to 41 percent by weight.

Organosilicon-comprising hydrogels are prepared by polymerizing a mixture comprising at least one organosilicon-comprising monomer and at least one hydrophilic monomer. In certain embodiments, a -comprising monomer which functions as a crosslinking agent (a crosslinker being defined as a monomer having multiple polymerizable functionalities) or a separate crosslinker may be employed. In certain embodiments hydrophobic crosslinkers are used. Examples of hydrophobic crosslinkers would include methacrylates such as ethylene glycol dimethacrylate (EGDMA) and allyl methacrylate (AMA). In certain embodiments hydrophilic crosslinkers might be used. Hydrophilic crosslinkers, for example methacrylamide crosslinkers such as Ma2D37, allow the incorporation of greater amounts of hydrophilic comonomers into the monomer mix than its hydrophobic methacrylate counterparts. This greater amount of hydrophilic comonomers provides a finished lens with higher water content and improved wettability. Amounts of cross-linker, either silicone-comprising, hydrophobic and hydrophilic, each type either separate or combined in any combination, would be present at between 0 to 76 percent by weight, 2 to 20 percent by weight or 5 to 13 percent by weight.

The ethylenically unsaturated free radical polymerizable group comprising polycarbosiloxane monomers of the application herein may be copolymerized with a wide variety of hydrophilic monomers to produce silicone hydrogel lenses. Suitable hydrophilic monomers include: unsaturated carboxylic acids, such as methacrylic and acrylic acids; acrylic substituted alcohols, such as 2-hydroxyethyl methacrylate and 2-hydroxyethyl acrylate; vinyl lactams, such as N-vinylpyrrolidone (NVP) and 1-vinylazonan-2-one; and acrylamides, such as methacrylamide and N,N-dimethylacrylamide (DMA). These hydrophilic monomers will be present in certain embodiments, separately or by combined weight, in amounts of between 0 to 60 percent by weight, between 20 to 45 percent by weight, between 0 to 48.6 percent by weight, between 0 to 30 percent by weight, between 0 to 25 percent by weight, between 0 to 9.5 percent by weight or between 2 to 7 percent by weight.

Other examples of silicone-comprising monomer mixtures which may be used within the spirit and teaching of this application include the following: vinyl carbonate and vinyl carbamate monomer mixtures as disclosed in U.S. Pat. Nos. 5,070,215 and 5,610,252 (Bambury et al); fluorosilicone monomer mixtures as disclosed in U.S. Pat. Nos. 5,321,108; 5,387,662 and 5,539,016 (Kunzler et al.); fumarate monomer mixtures as disclosed in U.S. Pat. Nos. 5,374,662; 5,420,324 and 5,496,871 (Lai et al.) and urethane monomer mixtures as disclosed in U.S. Pat. Nos. 5,451,651; 5,648,515; 5,639,908 and 5,594,085 (Lai et al.), all of which are commonly assigned to assignee herein Bausch & Lomb Incorporated, and the entire disclosures of which are incorporated herein by reference. Other suitable hydrophilic monomers will be apparent to one skilled in the art.

An organic diluent may be included in the initial monomeric mixture. As used herein, the term "organic diluent" encompasses organic compounds which minimize incompatibility of the components in the initial monomeric mixture and are substantially nonreactive with the components in the initial mixture. Additionally, the organic diluent serves to minimize phase separation of polymerized products produced by polymerization of the monomeric mixture. Also, the organic diluent will generally be relatively non-inflammable.

Contemplated organic diluents include alcohols such as tert-butanol (TBA), tert-amyl alcohol, hexanol and nonanol; diols, such as ethylene glycol; and polyols, such as glycerol. Preferably, the organic diluent is sufficiently soluble in the extraction solvent to facilitate its removal from a cured article during the extraction step. Other suitable organic diluents would be apparent to a person of ordinary skill in the art.

The organic diluent is included in an amount effective to provide the desired effect (for example, minimal phase separation of polymerized products). Generally, the diluent is included at 0 to 60% by weight of the monomeric mixture, with 1 to 40% by weight being more preferred, 2 to 30% by weight being even more preferred and 3 to 25% by weight being especially preferred.

According to the present process, the monomeric mixture, comprising at least one hydrophilic monomer, at least one ethylenically unsaturated free radical polymerizable group comprising polycarbosiloxane monomer and optionally the organic diluent, is shaped and cured by conventional methods such as static casting or spincasting.

Lens formation can be by free radical polymerization reactants such as are obtained by using initiators such as azobisisobutyronitrile (AIBN) or peroxide catalysts under conditions such as those set forth in U.S. Pat. No. 3,808,179, incorporated herein by reference; photoinitiation of free radical polymerization of the monomer mixture using photo initiators such as IRGACURE 819 (Bis(2,4,6-trimethylbenzoyl)-phenylphosphineoxide) and DAROCURE 1173 (2-Hydroxy-2-methyl-1-phenyl-propan-1-one) are also well known in the art and may be used in the process of forming an article as disclosed herein.

By careful selection of the appropriate wavelength of light to conduct photo polymerization of the monomer mix a finished product having desirable properties such as surface hydrophilicity and surface lubricity can result. Other reaction conditions important to photo polymerization would include incident light intensity, light exposure time and controlled atmosphere can also be critical to providing a successful commercial product. Suitable light intensity will depend upon polymerization conditions such as the mold material, monomer mix and initiator concentration ratio. For example, suitable intensities would range from 1.0 mW/cm2 to 25.0 mW/cm2. Similarly, light exposure time can vary, depending upon polymerization conditions. Therefore, light exposure time may range from one minute to 60 minutes. Control of atmospheric conditions for polymerizing contact lenses is well known in the art. Colorants and the like may be added prior to monomer polymerization.

Subsequently to polymerization conditions, a sufficient amount of unreacted monomer and, when present, organic diluent is removed from the cured article to improve the biocompatibility of the article. Release of non-polymerized monomers into the eye upon installation of a lens can cause irritation and other problems. Therefore, once the biomaterials formed from the polymerized monomer mix comprising the ethylenically unsaturated free radical polymerizable group comprising polycarbosiloxane monomers of the application herein and at least one of the other monomers disclosed herein are formed they are then extracted to prepare them for packaging and eventual use. Extraction is accomplished by exposing the polymerized materials to various solvents such as water, 2-propanol, etc. for varying periods of time. For example, one extraction process is to immerse the polymerized materials in water for about three minutes, remove the water and then immerse the polymerized materials in another aliquot of water for about three minutes, remove that aliquot of water and then autoclave the polymerized material in water, buffer solution or other packaging solution.

Surface structure and composition determine many of the physical properties and ultimate uses of solid materials. Characteristics such as wetting, friction, and adhesion or lubricity are largely influenced by surface characteristics. The alteration of surface characteristics is of special significance in biotechnical applications where biocompatibility is of particular concern. It should be remembered that in coating medical devices the term "surface" is not to be limited to meaning "at least one complete surface". Surface coverage does not have to be even or complete to be effective for surface functionality or surface treatment. Thus, it is desired to provide an organosilicon comprising hydrogel contact lens with an optically clear, hydrophilic surface film that will not only exhibit improved wettability, but which will generally allow the use of an organosilicon comprising hydrogel contact lens in the human eye for extended period of time. In the case of a organosilicon comprising hydrogel lens for extended wear, it may be further desirable to provide an improved organosilicon-comprising hydrogel contact lens with an optically clear surface film that will not only exhibit improved lipid and microbial behavior, but which will generally allow the use of a organosilicon-comprising hydrogel contact lens in the human eye for an extended period of time. Such a surface treated lens would be comfortable to wear in actual use and allow for the extended wear of the lens without irritation or other adverse effects to the cornea.

It may also be desirable to apply these surface enhancing coatings to implantable medical devices such as intraocular lens materials to reduce the attachment of lens epithelial cells to the implanted device and to reduce friction as the intraocular lens passes through an inserter into the eye. Therefore, if needed to produce a successful commercial product the polymerized materials may optionally be coated.

Methods of coating contact lenses and various types of coatings for contact lenses are well known to those of ordinary skill in the art. Methods of coating the substrate include dip coating of the substrate into a solution comprising the surface coating material. The solution comprising the surface coating material may contain substantially the surface coating material in solvent or may contain other materials such as cleaning and extracting materials. Other methods could include spray coating the device with the surface coating material. In certain embodiments, it may be necessary to use suitable catalysts, for example, a condensation catalyst. Alternatively, the substrate and the other surface coating material may be subjected to autoclave conditions. In certain embodiments, the substrate and the surface coating material may be autoclaved in the packaging material that will contain the coated substrate. Once the interaction between the substrate and the surface coating material has occurred, the remaining surface modifying agent could be substantially removed and packaging solution added to the substrate packaging material. Sealing and other processing steps then proceed as they usually do. Alternatively, the surface modifying agent could be retained in the substrate packaging material during storage and shipping of the substrate device to the end user.

Coatings for medical devices are typically oligomeric or polymeric and sized to provide suitable properties to the surface of the medical device to be coated. Coatings according to certain embodiments of the application herein will typically contain hydrophilic domain(s) showing good surface properties when the coating is associated with the substrate (i.e., the uncoated medical device). The hydrophilic domain(s) will comprise at least one hydrophilic monomer, such as, HEMA, glyceryl methacrylate, methacrylic acid ("MAA"), acrylic acid ("AA"), methacrylamide, acrylamide, N,N'-dimethylmethacrylamide, or N,N'-dimethylacrylamide; copolymers thereof; hydrophilic prepolymers, such as ethylenically unsaturated poly(alkylene oxide)s, cyclic lactams such as N-vinyl-2-pyrrolidone ("NVP"), or derivatives thereof. Still further examples are the hydrophilic vinyl carbonate or vinyl carbamate monomers. Hydrophilic monomers can be nonionic monomers, such as 2-hydroxyethyl methacrylate ("HEMA"), 2-hydroxyethyl acrylate ("HEA"), 2-(2-ethoxyethoxy)ethyl(meth)acrylate, glyceryl(meth)acrylate, poly(ethylene glycol(meth)acrylate), tetrahydrofurfuryl (meth)acrylate, (meth)acrylamide, N,N'-dimethylmethacrylamide, N,N'-dimethylacrylamide ("DMA"), N-vinyl-2-pyrrolidone (or other N-vinyl lactams), N-vinyl acetamide, and combinations thereof. Still further examples of hydrophilic monomers are the vinyl carbonate and vinyl carbamate monomers disclosed in U.S. Pat. No. 5,070,215, and the hydrophilic oxazolone monomers disclosed in U.S. Pat. No. 4,910,277. The contents of these patents are incorporated herein by reference. The hydrophilic monomer also can be an anionic monomer, such as 2-methacryloyloxyethylsulfonate salts. Substituted anionic hydrophilic monomers, such as from acrylic and methacrylic acid, can also be utilized wherein the substituted group can be removed by a facile chemical process. Non-limiting examples of such substituted anionic hydrophilic monomers include trimethylsilyl esters of (meth)acrylic acid, which are hydrolyzed to regenerate an anionic carboxyl group. The hydrophilic monomer also can be a cationic monomer selected from the group consisting of 3-methacrylamidopropyl-N,N,N-trimethyammonium salts, 2-methacryloyloxyethyl-N,N,N-trimethylammonium salts, and amine-comprising monomers, such as 3-methacrylamidopropyl-N,N-dimethyl amine. Other suitable hydrophilic monomers will be apparent to one skilled in the art.

Generally, a packaging system for the storage of an ophthalmic lens according to the present application includes at least a sealed container comprising one or more unused ophthalmic lenses immersed in an aqueous lens packaging solution. Preferably, the sealed container is a hermetically sealed blister-pack, in which a concave well comprising a contact lens is covered by a metal or plastic sheet adapted for peeling in order to open the blister-pack. The sealed container may be any suitable generally inert packaging material providing a reasonable degree of protection to the lens, preferably a plastic material such as polyalkylene, PVC, polyamide, and the like.

Organosilicon comprising substrates are generally hydrophobic. To improve the patient experience, especially as regards to comfort, it is not unusual to utilize a packaging solution or other method to reduce the hydrophobic character of the substrate or to provide a ready to use product with improved lubricity. The relative hydrophobic character of a surface can be measured by many means known to those of ordinary skill in the art. One example of a method of contact angle measurement is Sessile Drop technique. For organosilicon comprising substrates a high sessile drop contact angle is some indication of a relatively hydrophobic material (in the dry state). Based upon empirical observations, packaging solutions that provide a material having a sessile drop contact angle less than about 75 degrees are relatively hydrophilic and tend to easily slide about a hydrophobic surface such as that provided by a polystyrene Petri dish when a force such as applied by a hand held scalpel is used to slice the material (in this case a molded contact lens). Other packaging materials that provide a material having a sessile drop contact angle greater than about 75 degrees are relatively hydrophobic and tend to adhere to a hydrophobic surface such as that provided by a polystyrene Petri dish. It has surprisingly been discovered that when a organosilicon hydrogel material is packaged with a borate buffered polyphosphorylcholine solution the lens behaves as if it are packaged with a more hydrophobic material providing packaging solution (e.g., sessile drop contact angle greater than about 75 degrees) yet behaves as lubricious as a material packaged with a packaging solution that provides a material having a sessile drop contact angle less than about 75 degrees. Therefore a medical device packaged with a borate buffered polyphosphorylcholine solution is a preferred embodiment of the application herein.

Suitable packaging solution material selection will depend upon a particular lens formulation and is therefore somewhat broad in nature. Below are nonlimiting examples of representative cationic, anionic, and zwitterionic polymers or components, along with non-ionic surfactants and peptide-based materials which are useful in packaging solutions (depending upon the intended use).
Anionic Polymers
    Poly(acrylic acid)
    Poly(acrylamide-co-acrylic acid)
    Carboxymethylcellulose
Cationic Polymers
    Polymer JR
    Polymers having latent amines
Zwitterionic Components
    Phosphocholine
    Latent amino acids
Polypeptides
    Poly(glutamic acid)
    Poly(lysine)
Non-Ionic Surfactants
    Tetronic T1107
    Tetronic T908
    Hydroxypropyl methylcellulose
    Silicone surfactants (NVP-co-TRIS VC)
    Glycereth cocoate For the sake of simplicity the following discussion of packaging solutions will focus upon nonionic polymeric conditioning agents. It will be recognized that in general the selection of an appropriate packaging solution for the ophthalmic device formed from a polymerized monomer mix comprising monomers based on ethylenically unsaturated free radical polymerizable group comprising polycarbosiloxane monomers of the application herein is within the purview of one of ordinary skill in the art. However, as noted above, certain packaging solutions used with an organosilicon comprising device may be inventive in their own right.

Any suitable nonionic polymeric conditioning agent component may be employed in accordance with the present application provided that it functions as described herein and has no substantial detrimental effect on the contact lens being stored or on the wearer of the contact lens. This component is opthalmically acceptable at the concentrations used. Particularly useful components are those, which are water soluble, for example, soluble at the concentrations used in the presently useful liquid aqueous media.

These compounds condition the lens by providing one or more of the following attributes: increased viscosity for increased retention time on the lens; enhanced wetting of the lens surface; decreased surface friction (i.e., improved lubricity); or enhanced comfort of a contact lens by forming a cushioning film over the lens surface.

A class of nonionic, polymeric conditioning agents includes nonionic polysaccharides. Representative examples of suitable components for use herein include, but are not limited to, methylcellulose; hydroxyethylcellulose; hydroxypropylcellulose; hydroxypropylmethylcellulose; and methylhydroxyethylstarches.

Another class of nonionic, polymeric conditioning agents includes polyvinylalcohols and polyvinylpyrrolidones.

Another class of nonionic, polymeric conditioning agents includes polymers of PEO, including PEO homopolymers, and block copolymers of PEO and PPO. This class includes poloxamers and poloxamines, including those disclosed in U.S. Pat. No. 6,440,366.

The above classes of nonionic, polymeric conditioning agents are intended for illustrative purposes only and not to limit the scope of the present application. Such polymers are known to those of skill in the art.

Generally, the average molecular weight of nonionic, polymeric conditioning agent is a minimum of about 1 kDa and a maximum of about 700 kDa, more preferably, about 5 kDa to 500 kDa.

The amount of nonionic, polymeric conditioning agent employed is that amount effective to improve the surface properties of the ophthalmic device when combined with a nonionic, nonpolymeric polyol. Preferably the nonionic, polymeric conditioning agent is present in the packaging solution of the application in an amount of at least 0.01% w/v. The specific amount of such component used can vary widely depending on a number of factors, for example, the specific polymeric component and nonionic polyol being employed. Generally, the concentration of the nonionic, polymeric conditioning agent is from about 0.01 to about 10% w/w and preferably from about 0.5 to about 1.5% w/w.

In one embodiment, the nonionic, nonpolymeric polyol for use herein can be a nonionic polyol comprising 2 to about 12 carbon atoms and preferably 2 to 4 carbon atoms and from 2 to 8 hydroxyl groups. Representative examples of such nonionic polyols include glycerin, ethylene glycol, propylene glycol, sorbitol, mannitol, monosaccarides, disaccharides such as trehalose, and the like and mixtures thereof. In one embodiment, the nonionic polyol can be glycerin, ethylene glycol, sorbitol, mannitol, monosaccharides and mixtures thereof.

The amount of the nonionic, nonpolymeric polyol in the packaging solution will generally be an amount sufficient to form a more uniform coating on the surface of the lens when packaged in a packaging solution according to the present application. In general, the concentration of the nonionic polyol will ordinarily range from about 0.01 to about 10% w/w and preferably from about 0.1 to about 3.0% w/w.

The packaging solutions according to the present application are physiologically compatible. Specifically, the solution must be "opthalmically safe" for use with a lens such as a contact lens, meaning that a contact lens treated with the solution is generally suitable and safe for direct placement on the eye without rinsing, that is, the solution is safe and comfortable for daily contact with the eye via a contact lens that has been wetted with the solution. An opthalmically safe solution has a tonicity and pH that is compatible with the eye and includes materials, and amounts thereof, that are non-cytotoxic according to ISO standards and U.S. Food & Drug Administration (FDA) regulations. The solution should be sterile in that the absence of microbial contaminants in the product prior to release must be statistically demonstrated to the degree necessary for such products. The liquid media useful in the present application are selected to have no substantial detrimental effect on the lens being treated or cared for and to allow or even facilitate the present lens treatment or treatments. The liquid media are preferably aqueous-based. A particularly useful aqueous liquid medium is that derived from saline, for example, a conventional saline solution or a conventional buffered saline solution.

The pH of the present solutions should be maintained within the range of about 6.0 to about 8, and preferably about 6.5 to about 7.8. Suitable buffers may be added, such as: phosphate; borate; citrate; carbonate; tris-(hydroxyethyl) amino methane (TRIS); bis(2-hydroxyethyl)-amino-tris-(hydroxyethyl)amino alcohol (bis-tris); zwitterionic buffers such as N-[2-Hydroxy-1,1-bis(hydroxyethyl)ethyl]glycine (Trichina) and N-[2-Hydroxy-1,1-bis(hydroxyethyl)ethyl]glycine, MOPS; N—(Carbamoylmethyl)taurine (ACES); amino acids and amino acid derivatives; and mixtures thereof. Generally, buffers will be used in amounts ranging from about 0.05 to about 2.5 percent by weight, and preferably from about 0.1 to about 1.5 percent by weight of the solution. The packaging solutions of this application preferably contain a borate buffer, comprising one or more of boric acid, sodium borate, potassium tetra borate, potassium met borate or mixtures of the same.

If needed, the solutions of the present application may be adjusted with tonicity agents, to approximate the osmotic pressure of normal lacrimal fluids, which is equivalent to a 0.9 percent solution of sodium chloride or 2.5 percent of glycerol solution. The solutions are made substantially isotonic with physiological saline used alone or in combination, otherwise if simply blended with sterile water and made hypotonic or made hypertonic the lenses will lose their desirable optical parameters. Correspondingly, excess saline may result in the formation of a hypertonic solution, which will cause stinging, and eye irritation.

Examples of suitable tonicity adjusting agents include, but are not limited to, sodium and potassium chloride, dextrose, calcium and magnesium chloride and the like and mixtures thereof. These agents are typically used individually in amounts ranging from about 0.01 to about 2.5% w/v and preferably from about 0.2 to about 1.5% w/v. Preferably, the tonicity agent will be employed in an amount to provide a final osmotic value of at least about 200 mOsm/kg, preferably from about 200 to about 450 mOsm/kg, more preferably from about 250 to about 400 mOsm/kg, and most preferably from about 280 to about 370 mOsm/kg.

If desired, one or more additional components can be included in the packaging solution. Such additional component or components are chosen to impart or provide at least one beneficial or desired property to the packaging solution. Such additional components may be selected from components that are conventionally used in one or more ophthalmic device care compositions. Examples of such additional components include cleaning agents, wetting agents, nutrient agents, sequestering agents, viscosity builders, contact lens conditioning agents, antioxidants, and the like and mixtures thereof. These additional components may each be included in the packaging solutions in an amount effective to impart or provide the beneficial or desired property to the packaging solutions. For example, such additional components may be included in the packaging solutions in amounts similar to the amounts of such components used in other, e.g., conventional, contact lens care products.

Useful sequestering agents include, but are not limited to, disodium ethylene diamine tetra acetate, alkali metal hexametaphosphate, citric acid, sodium citrate and the like and mixtures thereof.

Useful antioxidants include, but are not limited to, sodium metabisulfite, sodium thiosulfate, N-acetylcysteine, butylated hydroxyanisole, butylated hydroxytoluene and the like and mixtures thereof.

The method of packaging and storing an ophthalmic lens according to the present application includes at least packaging the ophthalmic lens immersed in the aqueous contact lens packaging solution described above. The method may include immersing the ophthalmic lens in an aqueous contact lens solution prior to delivery to the customer/wearer directly following manufacture of the contact lens. Alternately, the packaging and storing in the solution of the present application may occur at an intermediate point before delivery to the ultimate customer (wearer) but following manufacture and transportation of the lens in a dry state, wherein the dry lens is hydrated by immersing the lens in the contact lens packaging solution. Consequently, a package for delivery to a customer may include a sealed container comprising one or more unused contact lenses immersed in an aqueous contact lens packaging solution according to the present application.

In one embodiment, the steps leading to the present ophthalmic device packaging system include (1) molding an ophthalmic device in a mold comprising at least a first and second mold portion, (2) removing the lens from the mold portions; (3) introducing the packing solution of this application and the ophthalmic lens into the container, and (4) sealing the container. Preferably, the method also includes the step of sterilizing the contents of the container. Sterilization may take place prior to, or most conveniently after, sealing of the container and may be effected by any suitable method known in the art, e.g., by balanced autoclaving of the sealed container at temperatures of about 120° C. or higher. Preferred packages are plastic blister packages, including a recess for receiving a contact lens and the package solution, where the recess is sealed with lidstock prior to sterilization of the package contents. Especially preferred packages would include a disposable package and package assembly for contact lenses. A single package comprises a flange with a well formed therein for holding a contact lens in solution. A flexible cover sheet extends over the flange and is sealed about the perimeter of the well to seal the lens and solution in the well. The cover sheet may be easily peeled from the flange by a user to access the lens held therein. First and second support structures are formed opposite each other and extend generally perpendicularly from the flange. The support structures are configured to stably support the package on a flat surface such as a table.

Each support structure includes a major wall and a minor wall lying in generally spaced, parallel planes to each other although the major and minor walls may interconnect or touch along one or more points thereof. In a preferred embodiment, the minor wall is located inwardly of a respective major wall.

A package assembly is also disclosed including a second package configured substantially the same as a first package wherein the first and second packages may be releasably attached to each other with the first and second support structures of each in meshing engagement with each other.

In certain embodiments, following extraction of unreacted monomers and any organic diluent, the shaped article, for example an RGP lens, is optionally machined by various processes known in the art. The machining step includes lathe cutting a lens surface, lathe cutting a lens edge, buffing a lens edge or polishing a lens edge or surface. The present process is particularly advantageous for processes wherein a lens surface is lathe cut, since machining of a lens surface is especially difficult when the surface is tacky or rubbery.

Generally, such machining processes are performed before the article is released from a mold part. After the machining operation, the lens can be released from the mold part and hydrated. Alternately, the article can be machined after removal from the mold part and then hydrated.

The following examples are provided to enable one skilled in the art to practice the application and are merely illustrative of the application. The examples should not be read as limiting the scope of the application as defined in the claims.

EXAMPLES

All solvents and reagents are obtained from commercially available sources and used as received.
Analytical Testing Methods
A 4502 Mechanical Tester MTS Instron is used to measure the modulus, tensile strength, percent elongation and tear strength of the lenses. Samples are tested in a water bath comprising borate buffered saline.

Captive bubble contact angle data is collected on a First Ten Angstroms FTA-1000 Drop Shape Instrument. All samples are rinsed in HPLC grade water prior to analysis in order to remove components of the packaging solution from the sample surface. Prior to data collection the surface tension of the water used for all experiments is measured using the pendant drop method. In order for the water to qualify as appropriate for use, a surface tension value of 70-72 dynes/cm is expected. All lens samples are placed onto a curved sample holder and submerged into a quartz cell filled with HPLC grade water. Receding and advancing captive bubble contact angles are collected for each sample.

The receding contact angle is defined as the angle measured in water as the air bubble is expanding across the sample surface (water is receding from the surface). The advancing contact angle is defined as the angle measured in water as the air bubble is retracting from the lens surface (water is advancing across the surface).

All captive bubble data is collected using a high speed digital camera focused onto the sample/air bubble interface. The contact angle is calculated at the digital frame just prior to contact line movement across the sample/air bubble interface.

ESI-TOF MS:

The electrospray (ESI) time of flight (TOF) MS analysis is performed on an Applied Biosystems Mariner instrument. The instrument operated in positive ion mode. The instrument is mass calibrated with a standard solution comprising lysine, angiotensinogen, bradykinin (fragment 1-5) and des-Pro bradykinin. This mixture provides a seven-point calibration from 147 to 921 m/z. The applied voltage parameters are optimized from signal obtained from the same standard solution. For exact mass measurements poly(ethylene glycol) (PEG), having a nominal $M_n$ value of 400 Da, is added to the sample of interest and used as an internal mass standard. Two PEG oligomers that bracketed the sample mass of interest are used to calibrate the mass scale. Samples are prepared as 30 μM solutions in isopropanol (IPA) with the addition of 2% by volume saturated NaCl in IPA. Samples are directly infused into the ESI-TOF MS instrument at a rate of 35 μL/min. A sufficient resolving power (6000 RP m/Δm FWHM) is achieved in the analysis to obtain the monoisotopic mass for each sample. In each analysis the experimental monoisotopic mass is compared to the theoretical monoisotopic mass as determined from the respective elemental compositions. In each analysis the monoisotopic mass comparison is less than 10 ppm error. It should be noted that uncharged samples have a sodium (Na) atom included in their elemental composition. This Na atom occurs as a necessary charge agent added in the sample preparation procedure. Some samples do not require an added charge agent since they contain a charge from the quaternary nitrogen inherent to their respective structure.

GC:

Gas chromatography is performed using a Hewlett Packard HP 6890 Series GC System. Purities are determined by integration of the primary peak and comparison to the normalized chromatograph.

NMR:

$^1$H-NMR characterization is carried out using a 400 MHz Varian spectrometer using standard techniques in the art. Samples are dissolved in chloroform-d (99.8 atom % D), unless otherwise noted. Chemical shifts are determined by assigning the residual chloroform peak at 7.25 ppm. Peak areas and proton ratios are determined by integration of baseline separated peaks. Splitting patterns (s=singlet, d=doublet, t=triplet, q=quartet, m=multiplet, br=broad) and coupling constants (J/Hz) are reported when present and clearly distinguishable.

Mechanical properties and Oxygen Permeability:

Modulus and elongation tests are conducted according to ASTM D-1708a, employing an Instron (Model 4502) instrument where the hydrogel film sample is immersed in borate buffered saline; an appropriate size of the film sample is gauge length 22 mm and width 4.75 mm, where the sample further has ends forming a dog bone shape to accommodate gripping of the sample with clamps of the Instron instrument, and a thickness of 200+50 microns.

Oxygen permeability (also referred to as Dk) is determined by the following procedure. Other methods and/or instruments may be used as long as the oxygen permeability values obtained therefrom are equivalent to the described method. The oxygen permeability of silicone hydrogels is measured by the polarographic method (ANSI Z80.20-1998) using an $O_2$ Permeometer Model 201T instrument (Createch, Albany, Calif. USA) having a probe comprising a central, circular gold cathode at its end and a silver anode insulated from the cathode. Measurements are taken only on pre-inspected pin-hole-free, flat silicone hydrogel film samples of three different center thicknesses ranging from 150 to 600 microns. Center thickness measurements of the film samples may be measured using a Rehder ET-1 electronic thickness gauge. Generally, the film samples have the shape of a circular disk. Measurements are taken with the film sample and probe immersed in a bath comprising circulating phosphate buffered saline (PBS) equilibrated at 35° C.+/−0.2°. Prior to immersing the probe and film sample in the PBS bath, the film sample is placed and centered on the cathode premoistened with the equilibrated PBS, ensuring no air bubbles or excess PBS exists between the cathode and the film sample, and the film sample is then secured to the probe with a mounting cap, with the cathode portion of the probe contacting only the film sample. For silicone hydrogel films, it is frequently useful to employ a Teflon polymer membrane, e.g., having a circular disk shape, between the probe cathode and the film sample. In such cases, the Teflon membrane is first placed on the pre-moistened cathode, and then the film sample is placed on the Teflon membrane, ensuring no air bubbles or excess PBS exists beneath the Teflon membrane or film sample. Once measurements are collected, only data with correlation coefficient value (R2) of 0.97 or higher should be entered into the calculation of Dk value. At least two Dk measurements per thickness, and meeting R2 value, are obtained. Using known regression analyses, oxygen permeability (Dk) is calculated from the film samples having at least three different thicknesses. Any film samples hydrated with solutions other than PBS are first soaked in purified water and allowed to equilibrate for at least 24 hours, and then soaked in PHB and allowed to equilibrate for at least 12 hours. The instruments are regularly cleaned and regularly calibrated using RGP standards. Upper and lower limits are established by calculating a +/−8.8% of the Repository values established by William J. Benjamin, et al., The Oxygen Permeability of Reference Materials, *Optom V is Sci* 7 (12s): 95 (1997), the disclosure of which is incorporated herein in its entirety:

| MATERIAL NAME | REPOSITORY VALUES | LOWER LIMIT | UPPER LIMIT |
|---|---|---|---|
| Fluoroperm 30 | 26.2 | 24 | 29 |
| Menicon EX | 62.4 | 56 | 66 |
| Quantum II | 92.9 | 85 | 101 |

ABBREVIATIONS

NVP 1-Vinyl-2-pyrrolidone

TRIS 3-Methacryloxypropyltris(trimethylsiloxy)silane

HEMA 2-Hydroxyethyl methacrylate v-64 2,2'-Azobis(2-methylpropionitrile)

EGDMA ethylene glycol dimethacrylate

BHT butylated hydroxytoluene

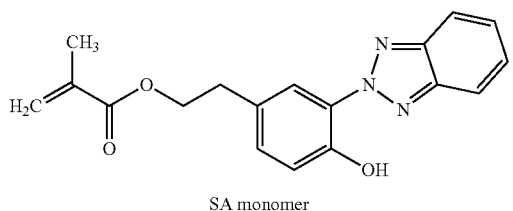

SA monomer

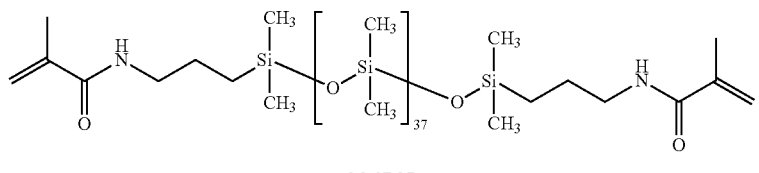

Ma2D37

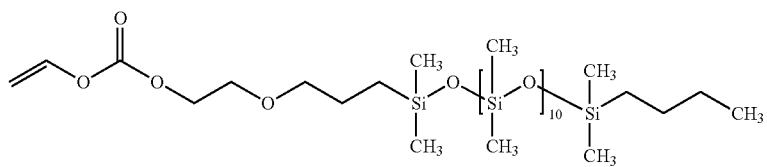

V1-MCR-C12

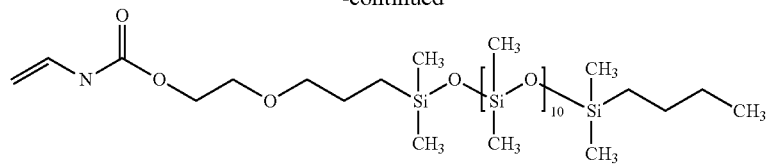

Vca-MCR-C12 or (Va-MCR-C12)

EDS Refers to a ring opened 2,2,5,5-tetramethyl-2,5-disila-1-oxacyclopentane unit.
This is also called an ethylene tetramethyl disiloxane unit.
PD5 2,2,5,5-tetramethyl-2,5-disila-1-oxacyclopentane
Triflic acid is CF3SO3H (trifloromethanesulfonic acid)

Unless otherwise specifically stated or made clear by its usage, all numbers used in the examples should be considered to be modified by the term "about" and to be weight percent.

Example 1

Typical Synthesis of $M2\text{-}EDS_n$

Synthesis of novel M2-EDSn derivatives is carried out by conventional cationic polymerization technique for the purpose of using them as polymeric cross linkers for our contact lens formulations. Thus when 2,2,5,5-tetramethyl-2,5-disila-1-oxacyclopentane (1) is treated with dimethacryloxybutyl-tetramethyldisiloxane (2) in presence of catalytic amount of triflic acid (3), compound $M2\text{-}EDS_n$ (4) is obtained in almost quantitative yield and the degree of polymerization is determined by NMR analysis.

Synthetic Scheme for $M2\text{-}EDS_n$

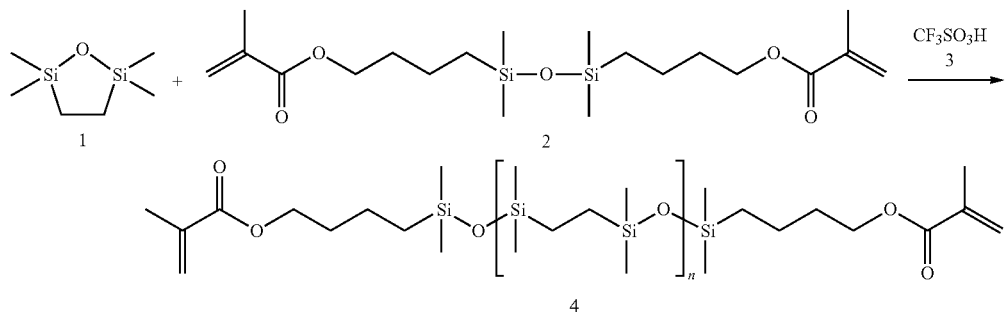

Example 2

Synthesis of $M2\text{-}EDS_{20}$ 2,2,5,5-tetramethyl-2,5-disila-1-oxacyclopentane (32 g, 0.2 mol) and dimethacryloxybutyl-tetramethyldisiloxane (4.14 g, 0.01 mol) are stirred in a round bottom flask (250 mL) under $N_2$ atmosphere. To this trifluoromethanesulfonic acid (100 μg) is added when an exothermic reaction is noted. After stirring for 10 min, dry cyclohexane (20 mL) is added under $N_2$ and stirring continued for 20 h at 25° C. Cyclohexane and other volatiles are then removed at 45° C./20 mm/Hg. To this sodium $NaHCO_3$ (500 mg) is added and stirring continued for 20 h at 25° C. Reaction mixture is then filtered over Celite. Filtrate is concentrated under vacuum to give clear oil in 34 g yield as the desired product and characterized by NMR, SEC and MALD/I showing about 20 condensed 2,2,5,5-tetramethyl-2,5-disila-1-oxacyclopentane ring open units. SEC analysis showed $M_n$=4175, $M_w$=7758 and $P_d$=1.85

Example 3

Synthetic Scheme for M2-Q2-EDSn

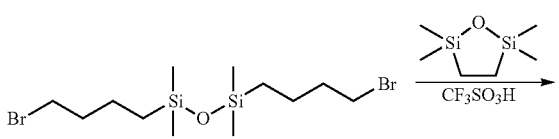

(I)

-continued

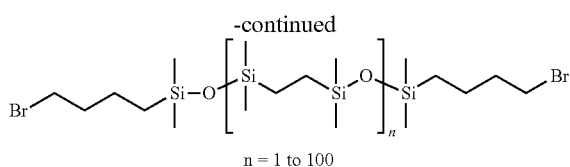

n = 1 to 100

500 mL 3 neck RB flask is soaked by 1 N HCl overnight, then rinsed by DI water and acetone, dried in 100° C. oven overnight. 1-3-bis(4-bromobutyl)tetramethyldisiloxane and PD5 are weighed into flask under stirring (200 rpm) from overhead mechanical stirrer and protected by drying tube (with drierite), then trifluoromethane sulfonic acid is added and stirred for 24 h at 25° C. To the above mixture is added sodium bicarbonate (1.75 g; Fisher, #096823) and the mixture is allowed to stir an additional 24 h at 25° C. The mixture is then filtered with slight positive nitrogen pressure through a press filter system equipped with 5 μm PTFE filter and Celite 503. The mixture is stirred with a magnetic stir bar and stripped for 4 h at 80° C. under 1.1 mmHg to afford clear liquid. NMR confirms the structure.

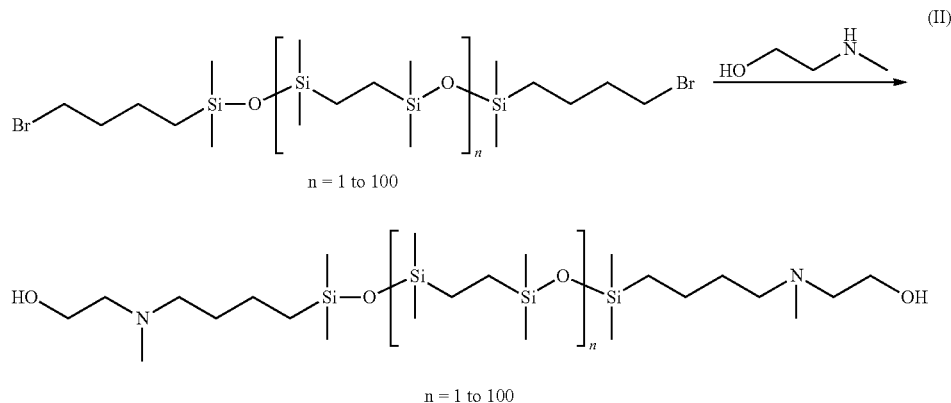

2-(methylamino)ethanol is added to a solution of (4-bromobutyl)poly(dimethylsilylethyldimethylsilyloxy)-dimethylsilylbutylbromide in 1,4-dioxane in 500 mL 3 neck RB flask equipped with overhead mechanical stirring and condenser, as well as thermometer. The reaction is protected by N$_2$ blanket. Heating mantle is used to heat the reaction mixture to 101° C. for 8 h. The solvent is stripped off by rotavap and the product is dissolved into 100 mL chloroform then transferred into 500 mL separation funnel. The unreacted 2-(methylamino)ethanol is drained from funnel before washing. Product is washed with 50/50 of brine and 10% bicarbonate (2×200 mL). Then dried by magnesium sulfate (Fisher 093474) 8.6 g with mechanical stirring for 3 h, filtered through Whatman filter paper #4, concentrated by rotavap and finally sent through 5 m PTFE filter membrane to afford clear liquid. NMR confirms the structure.

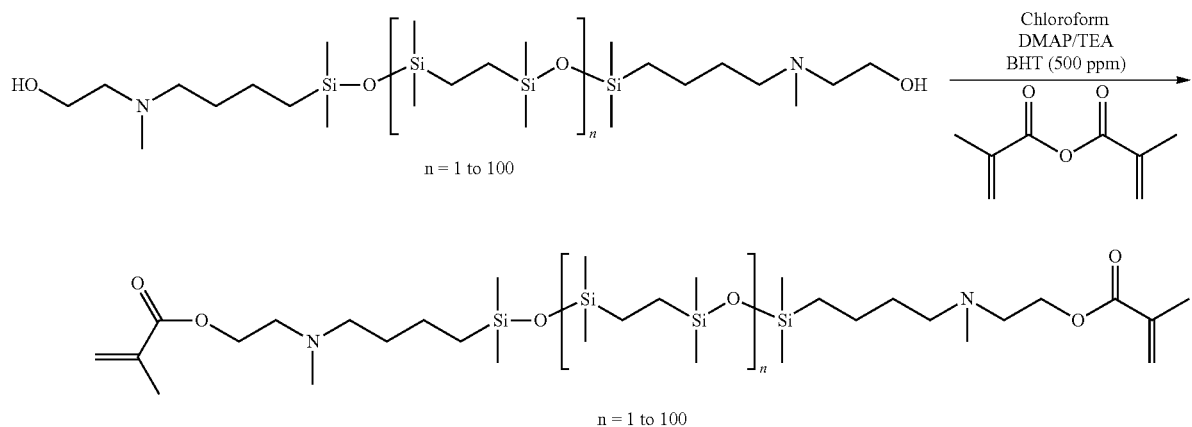

To the solution of (hydroxyethylmethyamino-4-butyl)poly(dimethylsilylethyldimethylsilyloxy)-dimethylsilylbutyl-methylaminoethanol in anhydrous chloroform (91 mL) in 500 mL 3 neck flask equipped with overhead mechanical stirring is added triethylamine (TEA) along with dimethylaminopyridine (DMAP) and 500 ppm of BHT as inhibitor. Methacrylic anhydride in chloroform (20 mL) is added dropwise from an addition funnel. The reaction system is sealed and protected by dry tube (with Drierite). The reaction is allowed to stir 15 h. Then DI water (140 mL) is introduced to the reaction and allowed to stir 57 hour. The reaction content is transferred into 1 L separation funnel and washed with 400 mL 50/50 of brine and 10% sodium bicarbonate (2×) followed by brine (2×200 mL). Product is then transferred into 1 neck 1 L flask with 50 g Amberlyst A-26(OH) Ion Exchange Resin (Aldrich #05207TE, Resin is washed by Chloroform 3×100 mL) for stirring 48 h. The product is filtered to remove resin bead by vacuum filtration and dried by magnesium sulfate for 2 h, filtered and concentrated by rotavap. The concentrated product is then filtered with slight positive nitrogen pressure through a pressure filter system equipped with 5 μm PTFE filter and Celite 503 to afford slight yellow liquid. NMR confirms the structure.

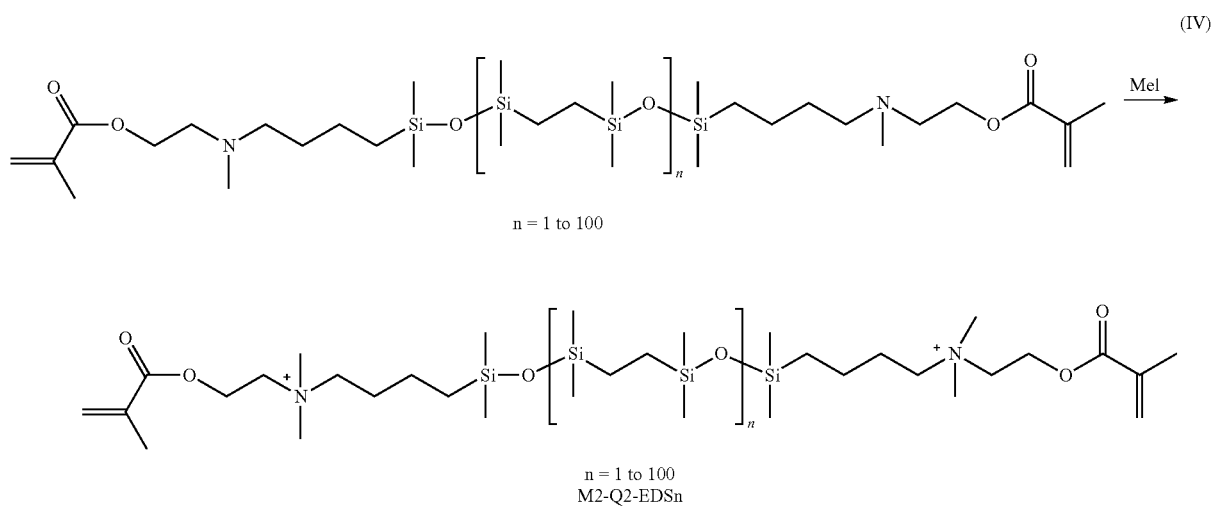

(Methyacryloxyethylmethyamino-4-butyl)poly(dimethylsilylethyldimethylsilyloxy)-dimethylsilylbutyl-methylaminomethacrylate is dissolved into 70 mL anhydrous THF and transferred into 500 mL 1 neck flask equipped with magnetic stirring bar. Iodomethane (2.2 mol eq.) is added to the above solution and the reaction is stirred at 45° C. for 8 hours, then solvent and excess iodomethane are removed by rotavap to afford a yellow, solid product. It is further purified under vacuum pump to provide product. NMR confirms the structure.

Example 4

Synthesis of Ma2-Q2-EDSn

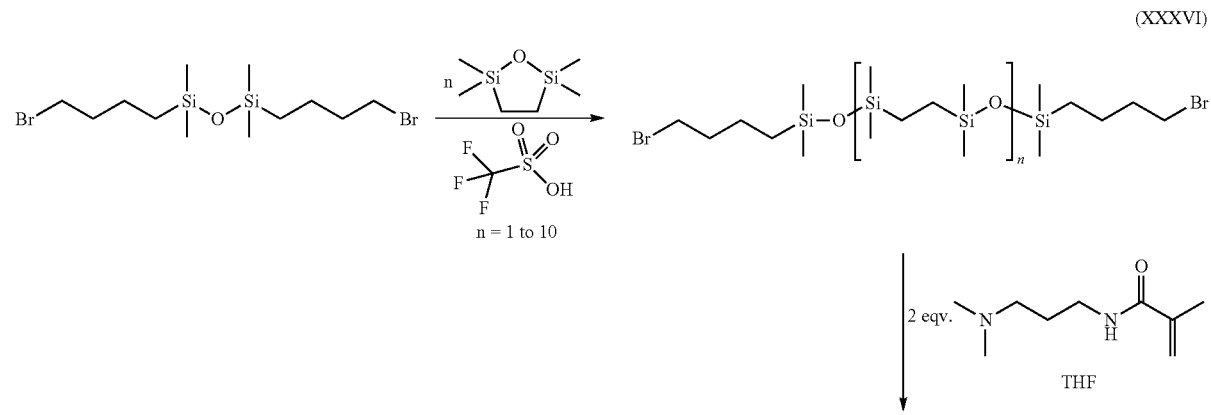

-continued

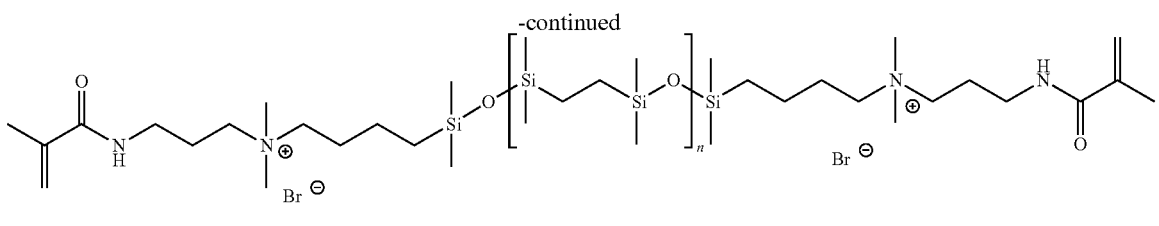

n = 1 to 10

Ma2-Q2-EDSn

To a round bottom flask charged with PD5, 1-3-bis(4-bromobutyl)tetramethyldisiloxane is added under nitrogen followed by addition of trifloromethanesulfonic acid. Reaction mixture is stirred for 24 h under $N_2$ at rt. Sodium bicarbonate is added to the reaction and allowed to stir for 24 h. The reaction mixture is then filtered over celite and concentrated using high vacuum. The compound is analyzed using NMR, MALDI and GPC. The polymer is then dissolved in THF and N-(3-(dimethylamino)propyl)methacrylamide is added dropwise to the reaction. The reaction mixture is allowed to reflux 16 h followed by removal of solvent and dried under vacuum to obtain the crosslinker. The final product is characterized by NMR, GC-MS and MALDI.

2,2,5,5-tetramethyl-2,5-disila-1-oxacyclopentane (14.4 g, 0.09 mol) is taken in 35 mL of dry cyclohexane under $N_2$ and stirred for 10 minutes at 25° C. To this lithium trimethylsilanolate (960 mg, 0.01 mol) is added with stirring. After 2 h dry THF (20 mL) is added and the reaction mixture continued to stir for 24 h at 25° C. Chlorodimethylsilylpropyloxy methacrylate (2.20 g, 0.01 mol) is then added and a color change is observed. Stirring is continued for 24 h more and the reaction mixture is then quenched with 10 mg $NaHCO_3$. Cyclohexane (10 mL) is added with continued stirring for 2 h more. The reaction mixture is then filtered over Celite. The filtrate is concentrated under vacuum to give clear oil in 16 g yield as the expected product M1-EDS9-TMS based on the method of preparation and characterized by NMR, SEC and MALDI.

Example 5

Synthesis of M1-EDS12-TMS 2,2,5,5-tetramethyl-2,5-disila-1-oxacyclopentane (19.2 g, 0.12 mol) is taken in 50 mL of dry cyclohexane under $N_2$ and stirred for 30 minutes at 25° C. To this mixture lithium trimethylsilanolate (960 mg, 0.01 mol) is added with stirring. After 2 h dry THF (20 mL) is added and the reaction mixture continued to stir for 24 h at 25° C. Chlorodimethylsilylpropyloxy methacrylate (2.20 g, 0.01 mol) is then added and a color change is observed. Stirring is continued for 24 h more and the reaction mixture is then filtered over Celite. The filtrate is concentrated under vacuum to give clear oil in 20 g yield as the expected product M1-EDS12-TMS based on the method of preparation and characterized by NMR, SEC and MALDI.

Example 6

Synthesis of M1-EDS15-TMS 2,2,5,5-tetramethyl-2,5-disila-1-oxacyclopentane (24 g, 0.15 mol) is taken in 60 mL of dry cyclohexane under $N_2$ and stirred for 10 minutes at 25° C. To this lithium trimethylsilanolate (960 mg, 0.01 mol) is added with stirring. After 2 h dry THF (20 mL) is added and the reaction mixture continued to stir for 24 h at 25° C. Chlorodimethylsilylpropyloxy methacrylate (2.20 g, 0.01 mol) is then added and a color change is observed. Stirring is continued for 24 h more and the reaction mixture is then quenched with 10 mg $NaHCO_3$. Cyclohexane (10 mL) is added with continued stirring for 2 h more. The reaction mixture is then filtered over Celite. The filtrate is concentrated under vacuum to give clear oil in 25 g yield as the expected product M1-EDS15-TMS based on the method of preparation and characterized by NMR, SEC and MALDI.

Example 7

Synthesis of M1-BIS-EDS3-TMS

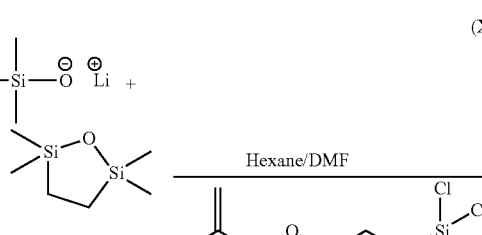

(XXXVII)

Lithium trimethyl silanolate (19.7 g, 0.2 mol) is suspended in anhydrous hexane (100 mL) in a 500 mL, round bottom flask is fitted with a mechanical stirrer, argon gas and a dropping funnel. A solution of 2,2,5,5-tetramethyl-2,5-disila-1-oxacyclopentane (32.07 g, 0.2 mol) in anhydrous hexane (100 mL), is quickly added to the flask with stirring. After an hour, the flask is cooled with an ice bath and DMF (50 mL) is added with continued stirring. After 4 h, 3-methacryloxypropyl methyldichlorosilane (29 g, 0.12 mol) is added dropwise to the reaction mixture. The reaction mixture is stirred further for 24 h at room temperature. Deionized water (50 mL) is then added to the flask with stirring. The organic layer is separated and dried over anhydrous sodium sulfate and filtered. The solvent is evaporated on a rotovap to give the desired product M1-BIS-EDS3-TMS in 40 g quantity as a clear, yellowish oil. The product is characterized by GC, GC/MS, IR and NMR.

Example 7

Synthesis of Dimethylammonium Methacrylamide (MA1-Q-EDS9-TMS)

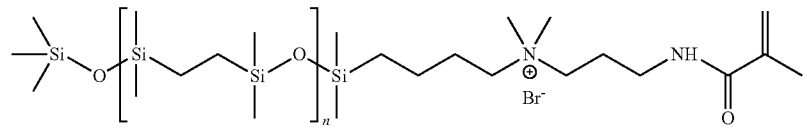

wherein n is 9.

2,2,5,5-tetramethyl-2,5-disila-1-oxacyclopentane (48 g, 0.3 mol) is taken in 55 mL of dry cyclohexane under $N_2$ and stirred for 30 minutes at 25° C. To this lithium trimethylsilanolate (4.8 g, 0.05 mol) is added with stirring. After 1 h dry THF (25 mL) is added and the reaction mixture continued to stir for 24 h at 25° C. Dimethylchlorosilane (5.1 g, 0.55 mol) is then added and a color change is observed. Stirring is continued for 3 h more and the reaction mixture is then filtered. Filtrate is concentrated under vacuum to give clear oil in 42 g yield as the expected product based on the method of preparation and characterized by NMR, SEC and MALDI. 28.0 g of this is used for hydrosilation by taking into toluene (30 mL) and adding 1-bromobutene (4 g, 0.03 mol) under $N_2$ atmosphere followed by the addition of platinum(0)1,3-divinyl-1,1,3,3-tetramethyl disiloxane complex 3 wt % solution in xylene (100 uL as catalyst). The reaction mixture is stirred for 4 h at 45-50° C. and then at 25° C. for 48 h. The reaction mixture is filtered over Celite using cotton plug, stripping off the solvent on rotovap and then high vacuum to gave a yellow oil in 27 g yield as the desired bromo compound trimethylsilyloxy-[poly(dimethylsilyl-ethyl-dimethylsilyloxy)]-dimethylsilylbutylbromide characterized by MALDI with n=–9 units.

6.6 g (0.004 mol) of the bromo compound and 680 mg (0.004 mol) of dimethylaminopropyl methacrylamide are mixed together and stirred under $N_2$ for 6 h at 25° C. Some exotherm is observed. Reaction mixture is subjected to high vacuum after 10 h to give the desired product MA1-Q-EDS9-TMS in almost quantitative yield and characterized by NMR and MALDI.

Example 8

Synthesis of Comparative Monofunctional M-MCR-C12

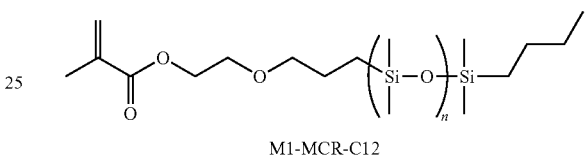

M1-MCR-C12 wherein n is 11.

Hydroxy ethoxypropyl terminated polydimethylsiloxane (50 grams, 0.048 mol) available from Gelest, Inc. (MCR-C12) is added to a 500 mL round bottom flask and dried via azeotropic distillation of toluene. To the flask is added anhydrous methylene chloride (200 mL) and triethylamine (17.12 g, 0.17 mol) and the reaction is stirred for 20 min. The reaction flask is fitted with an addition funnel which is charged with methacryloyl chloride (17.18 g, 0.16 mol) and an additional 85 mL of anhydrous methylene chloride. The contents of the addition funnel are added to the reaction mixture dropwise at which time the addition funnel is exchanged with a reflux condenser. The reaction is then brought to reflux for 4 h. After cooling the reaction mixture is filtered and placed in a separatory funnel where it is washed 2 times with 0.1 N HCl (150 mL); 2 times with sodium bicarbonate solution (150 mL) and 2 times with brine solution (150 mL). The organic layer is then stirred with 10 g of decolorizing carbon and 10 g of silica gel for 24 h and is then filtered and brought to dryness on a rotovap. The reaction yielded 45 g of a clear, yellow oil M1-MCR-C12 that is characterized by GC, NMR, and MALDI.

Example 9

Synthesis of Comparative Monofunctional MCA1-MCR-C12

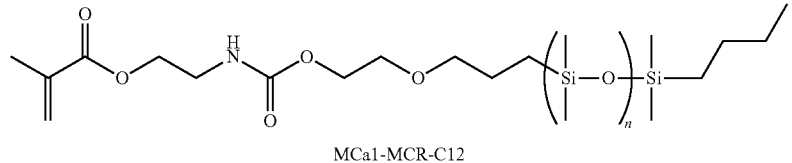

MCa1-MCR-C12 wherein n is 11.

Hydroxy ethoxypropyl terminated polydimethylsiloxane (200 g, 0.193 mol) available from Gelest, Inc. (MCR-C12) is added to a 2 L round bottom flask and dried via azeotropic distillation of toluene. To the flask is added anhydrous methylene chloride (500 mL) and dibutyltin dilaurate (0.474 g, 0.0007 mol). The reaction flask is fitted with an addition funnel which is charged with 2-isocyanatoethyl methacrylate (45.0 g, 0.290 mol) and an additional 100 mL of anhydrous methylene chloride. The contents of the addition funnel is then added to the reaction mixture dropwise and the reaction is stirred for 48 h. 50 g of silica gel (EMD Silica gel 60) is then added to the reaction mixture and stirred for 24 h to scavenge excess isocyanatoethyl methacrylate. The reaction mixture is then filtered and concentrated on a rotovap yielding 210 g of a clear oil MCA1-MCR-C12 that is characterized by GC, NMR, and MALDI.

TABLE 1

Examples 10-31. Formulation of various EDS based monomers and comparative examples

| Example | Ma2D37 Methacrylamide Crosslinker | TRIS [tris(trimethylsiloxy)-silylpropyl methacrylate] | N-Vinyl Pyrolidone | N,N-Dimethylacrylamide | 2-Hydroxyethyl methacrylate | Hexanol | M1-MCR-C12 | MCa1-MCR-C12 |
|---|---|---|---|---|---|---|---|---|
| 10 | 9.5 | 35.5 | 30.8 | 4.7 | 4.7 | 4.7 | 9.5 | X |
| 11 | 9.5 | 35.5 | 30.8 | 4.7 | 4.7 | 4.7 | X | 9.5 |
| 12 | 9.5 | 35.5 | 30.8 | 4.7 | 4.7 | 4.7 | X | X |
| 13 | 9.5 | 35.5 | 30.8 | 4.7 | 4.7 | 4.7 | X | X |
| 14 | 9.5 | 35.5 | 30.8 | 4.7 | 4.7 | 4.7 | X | X |
| 15 | 9.5 | 35.5 | 30.8 | 4.7 | 4.7 | 4.7 | X | X |
| 16 | 9.5 | 35.5 | 30.8 | 4.7 | 4.7 | 4.7 | X | X |
| 17 | 0.0 | 29.9 | 25.9 | 4.0 | 4.0 | 19.9 | X | X |
| 18 | 0.0 | 32.5 | 28.1 | 4.3 | 4.3 | 13.0 | X | X |
| 19 | 9.5 | 35.5 | 30.8 | 4.7 | 4.7 | 4.7 | X | X |
| 20 | 9.5 | 35.5 | 30.8 | 4.7 | 4.7 | 4.7 | X | X |
| 21 | 9.5 | 35.5 | 30.8 | 4.7 | 4.7 | 4.7 | X | X |
| 22 | 9.5 | 35.5 | 30.8 | 4.7 | 4.7 | 4.7 | X | X |
| 23 | 9.5 | 35.5 | 30.8 | 4.7 | 4.7 | 4.7 | X | X |
| 24 | 9.5 | 35.5 | 30.8 | 4.7 | 4.7 | 4.7 | X | X |
| 25 | 9.5 | 35.5 | 30.8 | 4.7 | 4.7 | 4.7 | X | X |
| 26 | 9.5 | 35.5 | 30.8 | 4.7 | 4.7 | 4.7 | X | X |
| 27 | 9.5 | 35.5 | 30.8 | 4.7 | 4.7 | 4.7 | X | X |
| 28 | 9.5 | 35.5 | 30.8 | 4.7 | 4.7 | 4.7 | X | X |
| 29 | 9.5 | 35.5 | 30.8 | 4.7 | 4.7 | 4.7 | X | X |
| 30 | 9.5 | 35.5 | 30.8 | 4.7 | 4.7 | 4.7 | X | X |
| 31 | 9.5 | 35.5 | 30.8 | 4.7 | 4.7 | 4.7 | X | X |

| Example | M1-EDS7-TMS | M1-EDS6-TMS | M1-EDS9-TMS | M1-EDS12-TMS | M1-EDS15-TMS | M2-EDS23 | VMa2-EDS20 | VM2-EDS20 | Ma2-EDS20 | VMa2-D12-EDS10 | VM2-D12-EDS10 | Ma2-D12-EDS10 | M2-D12-EDS10 |
|---|---|---|---|---|---|---|---|---|---|---|---|---|---|
| 10 | X | X | X | X | X | X | X | X | X | X | X | X | X |
| 11 | X | X | X | X | X | X | X | X | X | X | X | X | X |
| 12 | 9.5 | X | X | X | X | X | X | X | X | X | X | X | X |
| 13 | X | 9.5 | X | X | X | X | X | X | X | X | X | X | X |
| 14 | X | X | 9.5 | X | X | X | X | X | X | X | X | X | X |
| 15 | X | X | X | 9.5 | X | X | X | X | X | X | X | X | X |
| 16 | X | X | X | X | 9.5 | X | X | X | X | X | X | X | X |
| 17 | X | X | 8.0 | X | X | 8.0 | X | X | X | X | X | X | X |
| 18 | X | X | 8.7 | X | X | X | X | X | X | X | X | X | X |
| 19 | X | X | X | X | X | X | X | X | X | X | X | X | X |
| 20 | X | X | X | X | X | X | X | X | X | X | X | X | X |
| 21 | X | X | X | X | X | X | X | X | X | X | X | X | X |
| 22 | X | X | X | X | X | X | X | X | X | X | X | X | X |
| 23 | X | X | X | X | X | X | X | X | X | X | X | X | X |
| 24 | X | X | X | X | X | X | 8.0 | X | X | X | X | X | X |
| 25 | X | X | X | X | X | X | X | 8.0 | X | X | X | X | X |

TABLE 1-continued

Examples 10-31. Formulation of various EDS based monomers and comparative examples

| 26 | X | X | X | X | X | X | X | X | 8.0 | X | X | X | X |
| 27 | X | X | X | X | X | X | X | X | X | 8.0 | X | X | X |
| 28 | X | X | X | X | X | X | X | X | X | X | 8.0 | X | X |
| 29 | X | X | X | X | X | X | X | X | X | X | X | 8.0 | X |
| 30 | X | X | X | X | X | X | X | X | X | X | X | X | 8.0 |
| 31 | X | X | X | X | X | X | X | X | X | X | X | X | X |

| Example | M2-D27-EDS10 | Ma2-Q2-EDS10 | M1-Bis-D3-TMS | M1-Bis-EDS3-TMS | Ma1-Q-EDS9-TMS | M1-MCR-C12 | MCA1-MCR-C12 | Darocur 1173 | IMVT (concentration in ppm) |
|---|---|---|---|---|---|---|---|---|---|
| 10 | X | X | X | X | X | X | X | 0.47 | 90 |
| 11 | X | X | X | X | X | X | X | 0.47 | 90 |
| 12 | X | X | X | X | X | X | X | 0.47 | 90 |
| 13 | X | X | X | X | X | X | X | 0.47 | 90 |
| 14 | X | X | X | X | X | X | X | 0.47 | 90 |
| 15 | X | X | X | X | X | X | X | 0.47 | 90 |
| 16 | X | X | X | X | X | X | X | 0.47 | 90 |
| 17 | X | X | X | X | X | X | X | 0.47 | 90 |
| 18 | 8.7 | X | X | X | X | X | X | 0.47 | 90 |
| 19 | X | X | 9.5 | X | X | X | X | 0.47 | 90 |
| 20 | X | X | X | 9.5 | X | X | X | 0.47 | 90 |
| 21 | X | X | X | X | 9.5 | X | X | 0.47 | 90 |
| 22 | X | X | X | X | X | 9.5 | X | 0.47 | 90 |
| 23 | X | X | X | X | X | X | 9.5 | 0.47 | 90 |
| 24 | X | X | X | X | X | X | X | 0.47 | 90 |
| 25 | X | X | X | X | X | X | X | 0.47 | 90 |
| 26 | X | X | X | X | X | X | X | 0.47 | 90 |
| 27 | X | X | X | X | X | X | X | 0.47 | 90 |
| 28 | X | X | X | X | X | X | X | 0.47 | 90 |
| 29 | X | X | X | X | X | X | X | 0.47 | 90 |
| 30 | X | X | X | X | X | X | X | 0.47 | 90 |
| 31 | X | 8.0 | X | X | X | X | X | 0.47 | 90 |

Note:
The amounts presented in the table above are weight percentages in the formulation. Tint level is in ppm.

Monomer Mix Preparation Procedure:

For examples 10-31 and 35 to 39, the specific monomer mixes set forth are prepared according to Table 1 above and Table 2 below by weighing out various weight percentages of the components. Monomer mix is dispensed between polypropylene molds and prepared as lenses or flats in the case of Dk samples. Polymerization is carried out under UV light (~350 nm) for a period of two hours. After polymerization, the lenses or flats are released from the molds using 33% IPA in water and then extracted in 100% IPA for 4 h. Lenses/flats are then placed in deionized water for 30 min and packaged in vials comprising 4 mL of borate buffered saline (BBS).

Example 32

Improved Lubricity by Coating with Phosphatidyl Choline

For each example 10-31, a 0.5% solution of polymer in BBS is prepared by adding 1.25 g of polymer to BBS. The total volume of the solution is 250 mL. The pH of the solutions is 7.2. The test solution is poly(phosphatidycholine). Comparative solutions comprising separately poly(acrylic acid)-450,000 g/mol, tetronic T1107, tetronic T908, HPMC and Polymer JR are also prepared. All solutions are made at a concentration of 0.5% in BBS and pH is adjusted to 7.2 if needed (by standard techniques known in the art).

For lens testing, 4.5 mL of each solution is added to a glass autoclave vial. An organosilicon-comprising lens is placed in each vial and the system is capped with a Teflon-coated crimp cap. Each system is then autoclaved (121° C. for 30 min). The packaged lens is then removed from the package and rinsed with DI water. The rinsed lens is then placed on a polystyrene Petri dish and sectioned with a scalpel in order to cause the lens to lie flat.

Example 33

Synthetic Scheme for M2-EDS2

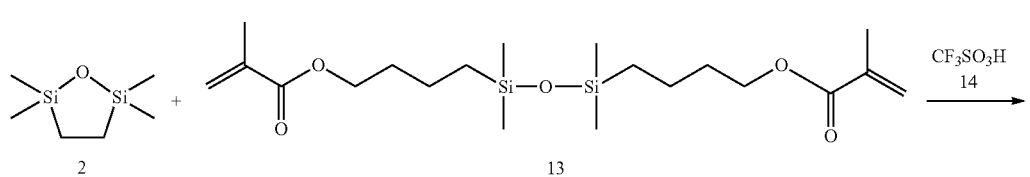

(XXXVIII)

-continued

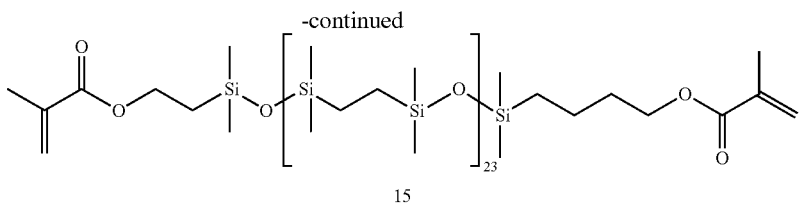
15

Synthesis of novel M2-EDSn derivatives is carried out by conventional cationic polymerization technique for the purpose of using them as polymeric cross linkers for our contact lens formulations. Thus when (2) is treated with dimethacryloxybutyl-tetramethyldisiloxane (13) in presence of catalytic amount of triflic acid (14), compound M2-EDS$_{23}$ (15) is obtained in almost quantitative yield and the degree of polymerization is determined by NMR analysis.

Example 34

Synthesis of M2-EDS$_{20}$

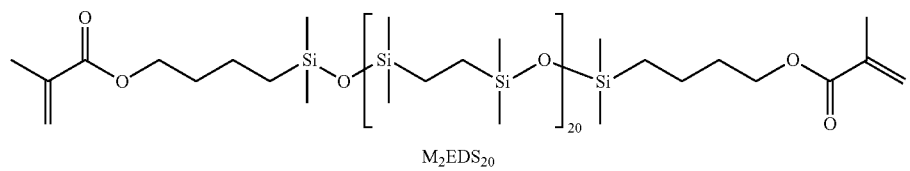

M$_2$EDS$_{20}$ 2,2,5,5-tetramethyl-2,5-disila-1-oxacyclopentane (32 g, 0.2 mol) and dimethacryloxybutyl-tetramethyldisiloxane (4.14 g, 0.01 mol) are stirred in a round bottom flask (250 mL) under N$_2$ atmosphere. To this trifluoromethanesulfonic acid (100 µg) is added when an exothermic reaction is noted. After stirring for 10 min, dry cyclohexane (20 mL) is added under N$_2$ and stirring continued for 20 h at 25° C. Cyclohexane and other volatiles are then removed at 45° C./20 mmHg. To this NaHCO$_3$ (500 mg) is added and stirring continued for 20 h at 25° C. Reaction mixture is then filtered over Celite. Filtrate is concentrated under vacuum to give clear oil in 34 g yield as the desired product and characterized by NMR, SEC and MALDI showing about 20 condensed 2,2,5,5-tetramethyl-2,5-disila-1-oxacyclopentane ring open units. SEC analysis showed M$_n$=4175, M$_w$=7758 and P$_d$=1.85

TABLE 2

EXAMPLES 35-39

| | | Example No. | | | | |
|---|---|---|---|---|---|---|
| | | Thirty five | Thirty six | Thirty seven | Thirty eight | Thirty nine |
| | | | | Formulation ID# | | |
| | | 2873-GLO-4a | 2873-GLO-4b | 2873-GLO-4c | 2873-GLO-4d | 2873-GLO-4e |
| | | Units (wt. in g, wt. %, parts, etc.) | | | | |
| Formulation components | Lot # | wt. % | wt. % | wt. % | wt. % | wt. % |
| Ma2D37 | 2759-138 | 8.40 | | | | |
| M2-EDS-23 | 2790-51 | | 8.48 | 7.84 | | |
| M2-D27-EDS-10 | 2790-52 | | | | 8.53 | 7.81 |
| Hexanol | 14723R | 13.03 | 13.16 | 20.04 | 13.15 | 19.85 |
| M1-MCR-C12 | 9B-14122 | 8.48 | 8.53 | 8.25 | 8.31 | 7.92 |
| TRIS | 100-0308NTL | 32.28 | 32.37 | 29.84 | 32.34 | 29.91 |
| NVP | 09607AJ | 28.15 | 28.11 | 25.70 | 28.17 | 25.84 |
| DMA | 08327LH | 4.56 | 4.52 | 4.02 | 4.53 | 4.05 |
| HEMA | ULA # 1 | 4.63 | 4.35 | 3.92 | 4.51 | 4.20 |
| DC 1173 | 1112PC | 0.47 | 0.49 | 0.40 | 0.47 | 0.41 |
| Modulus (gm/sqmm) | | 73 | 75 | 65 | 48 | 57 |
| Tear (gm/mm) | | 6 | 8 | 10 | 6 | 7 |
| Percent Water Content | | 45.6 | 42.4 | 41.0 | 44.7 | 44.3 |
| DK (Barrers) | | 89 | 92 | 93 | 87 | 102 |

TABLE 2-continued

EXAMPLES 35-39

| | | Example No. | | | | |
|---|---|---|---|---|---|---|
| | | Thirty five | Thirty six | Thirty seven | Thirty eight | Thirty nine |
| | | | | Formulation ID# | | |
| | | 2873-GLO-4a | 2873-GLO-4b | 2873-GLO-4c | 2873-GLO-4d | 2873-GLO-4e |
| | | | | Units (wt. in g, wt. %, parts, etc.) | | |
| Formulation components | Lot # | wt. % | wt. % | wt. % | wt. % | wt. % |
| Clarity (Use Clear, Hazy, Cloudy) | | | | | | |
| Mix | | Clear | Clear | Clear | Clear | Clear |
| Lens/Film after casting | | Clear | Clear | Clear | Hazy | Clear |
| Lens/Film after extraction | | Clear | Clear | Clear | Hazy | Clear |
| Lens/Film after autoclave | | 4/3 | 3/3 | 2/2 | 1/1 | 3/3 |
| Lens Dry release? (Use Y, N, NA) | | | | | | |
| Lens Wet release? (Use Y, N, NA) | | Wet | Wet | Wet | Wet | Wet |
| Wet release conditions, e.g. 33% IPA | | 33% IPA | 33% IPA | 33% IPA | 33% IPA | 33% IPA |

PREFERRED EMBODIMENTS

Disclosed in certain preferred embodiments of the application herein is:

1. A monomer comprising a polycarbosiloxane monomer.
2. An at least di-ethylenically unsaturated free radical polymerizable monomer comprising a polycarbosiloxane monomer.
3. A monomer mix comprising a polycarbosiloxane monomer.
4. The monomer mix of preferred embodiment of 3 wherein the polycarbosiloxane monomer further comprises at least two ethylenically unsaturated free radical polymerizable groups.
5. A polycarbosiloxane monomer further comprising at least two ethylenically unsaturated free radical polymerizable groups capable of polymerization to form polymeric compositions having the following structure:

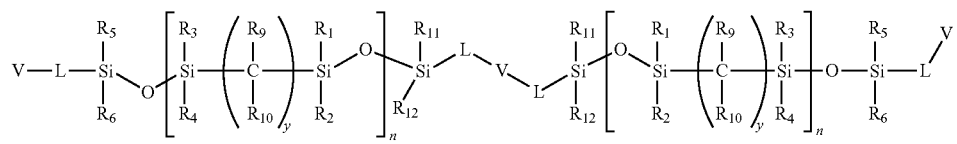

Wherein L is not a bond and V is not a monovalent ethylenic moiety.

6. A monomer having a structural formula selected from the group consisting of

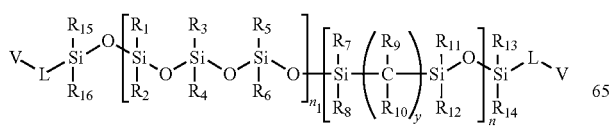
(I)

wherein $R_1$, $R_2$, $R_3$, $R_4$, $R_5$, $R_6$, $R_7$, $R_8$, $R_{11}$, $R_{12}$, $R_{13}$, $R_{14}$, $R_{15}$, and $R_{16}$ are independently a monovalent atom or group including H, alkyl, halo alkyl, heteroalkyl, cyclo alkyl, heterocyclo alkyl, alkenyl, halo alkenyl, or aromatic; as would be understood by one of ordinary skill in the art, $R_9$ and $R_{10}$ may not be present when monomers of formula (I) comprise -[silyl-alkenyl-siloxy]- units and when present in a monomer comprising -[silyl-alky-siloxy]- units are independently a monovalent atom or group including H, alkyl, alkene, alkyne; wherein at least one of $R_9$ or $R_{10}$ is hydrogen; y is 2-7; n is 1-100; $n^1$ is 0-10; L is the same or different and is a divalent linker group or a bond; and V is an ethylenically unsaturated free radical polymerizable monovalent group;

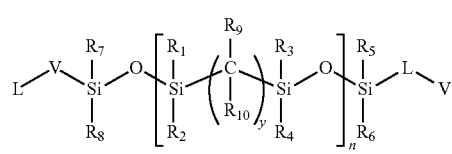
(II)

wherein L, V, $R_1$, $R_2$, $R_3$, $R_4$, $R_5$, $R_6$, $R_7$, $R_8$, $R_9$, $R_{10}$, y and n are as defined above. As would be understood by one of ordinary skill in the art, $R_9$ and $R_{10}$ may not be present when monomers of formula (II) comprise -[silyl-alkenyl-siloxy]- units and when present in a monomer comprising a -[silyl-alkenyl-siloxy]- unit are independently a monovalent atom or group including H, alkyl, alkene, alkyne; wherein at least one of $R_9$ or $R_{10}$ is hydrogen;

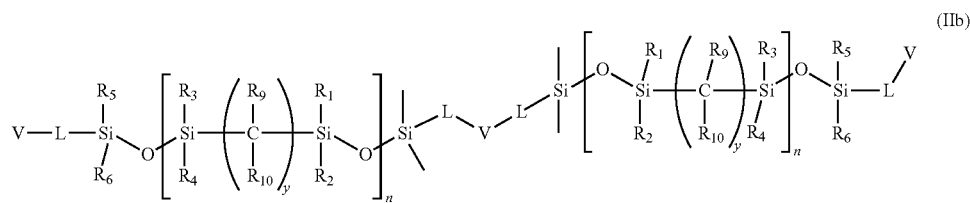

(IIb)

wherein L is the same or different and is a linker group or a bond and V is the same or different and is an ethylenically unsaturated polymerizable group, $R_1$, $R_2$, $R_3$, $R_4$, $R_5$, $R_6$ and $R_9$ are independently H, alkyl, halo alkyl, cyclo alkyl, helerocyclo alkyl, alkenyl, halo alkenyl, or aromatic, $R_7$ and $R_8$ are independently H or alkyl wherein at least one of $R_7$ or $R_8$ is hydrogen, y is 2-7 and n is 1-100;

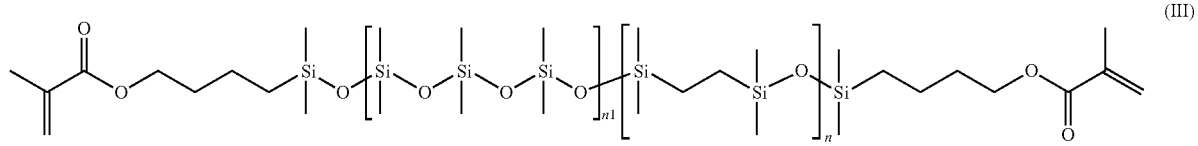

(III)

wherein n and $n^1$ are as defined above;

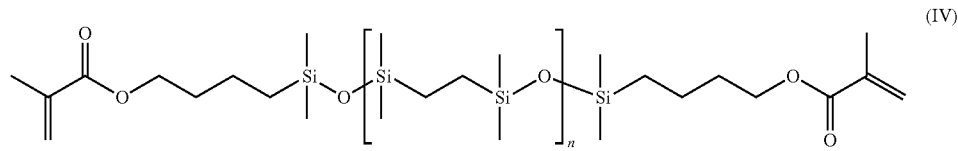

(IV)

wherein n is 1-100, preferably n is 2-80, more preferably n is 3-20, most preferably n is 5-15;

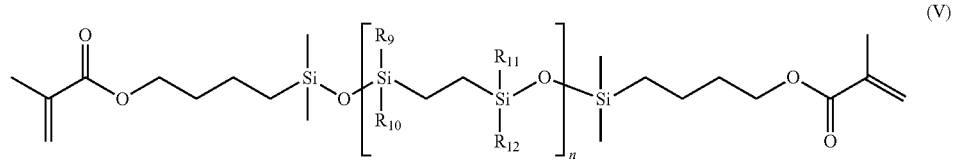

(V)

wherein $R_9$, $R_{10}$, $R_{11}$, and $R_{12}$ are as defined above;

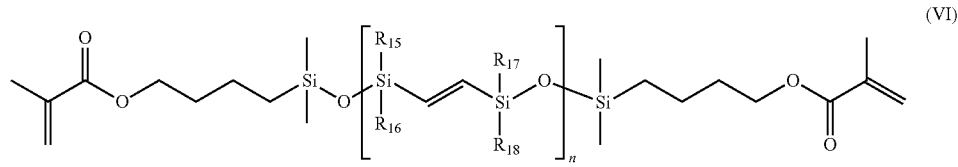

(VI)

wherein $R_{15}$, $R_{16}$, $R_{17}$ and $R_{18}$ are a monovalent atom or group including hydrogen, or monovalent alkyl, alkene or alkyne groups and at least one of $R_{15}$, $R_{16}$, $R_{17}$ and $R_{18}$ is hydrogen;

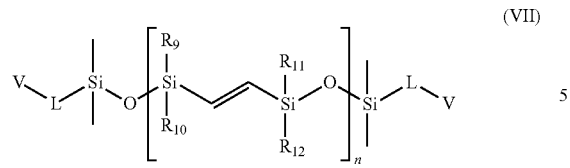
wherein V, L, R₉, R₁₀, R₁₁, and R₁₂ are as defined above;
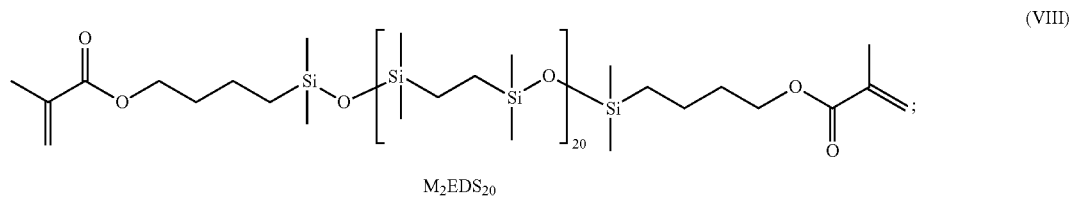
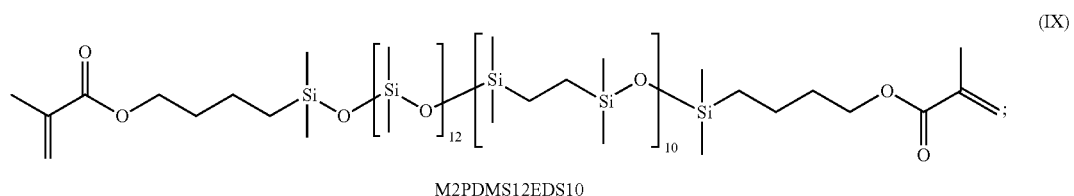
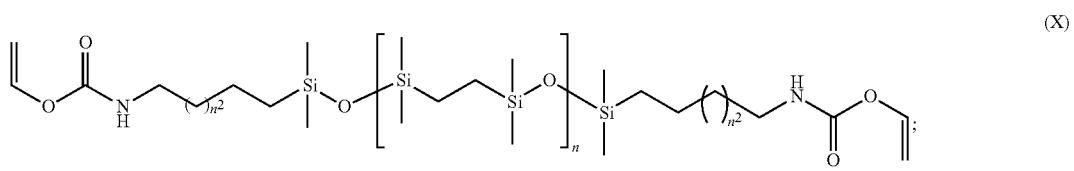
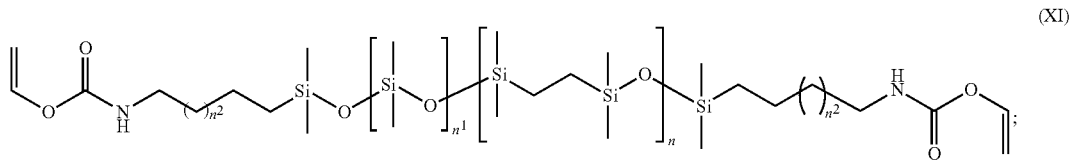
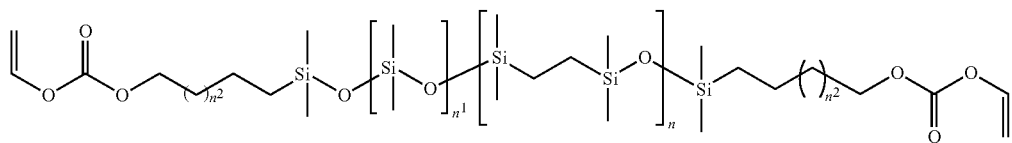
wherein n and n¹ are as defined above and n² is 0 to 10;
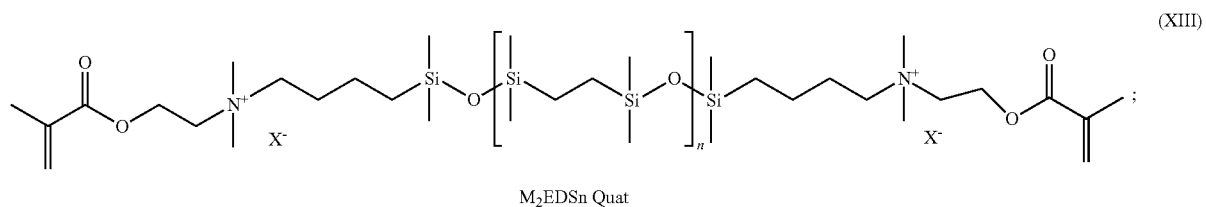
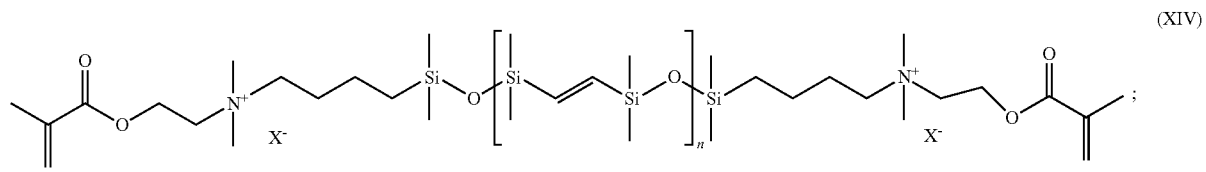

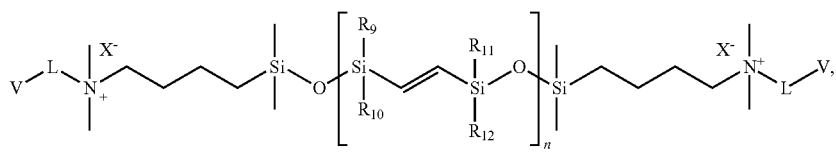
(XV)

wherein n is as defined above; X⁻ is a counter ion to provide an overall neutral charge and V, L, $R_9$, $R_{10}$, $R_{11}$, and $R_{12}$ are as defined above;

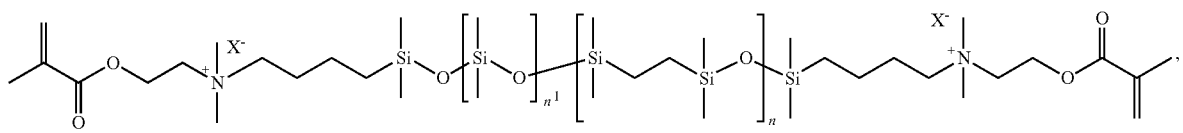
(XVI)

Wherein n and $n^1$ are as defined above and X⁻ is a counter ion to provide an

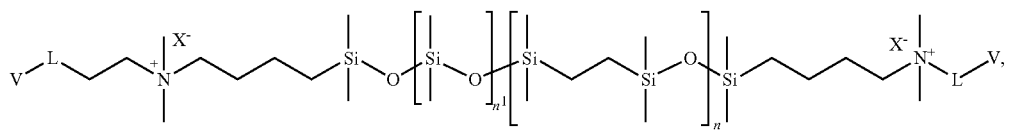
(XVII)

Wherein n, $n^1$, V and L are as defined above and X⁻ is a counter ion to provide an overall neutral charge;

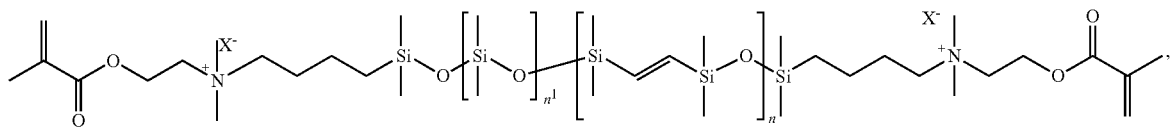
(XVIII)

Wherein n and $n^1$ are as defined above and X⁻ is a counter ion to provide an overall neutral charge;

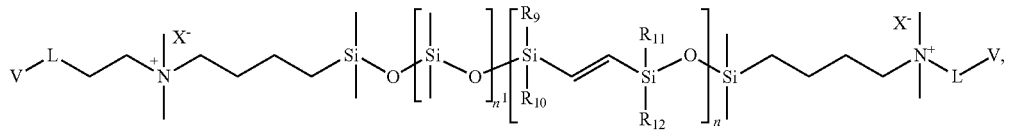
(XIX)

Wherein n, $n^1$, V, L, $R_9$, $R_{10}$, $R_{11}$, and $R_{12}$ are as defined above;

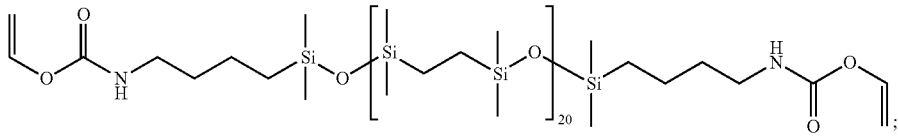
(XX)

VMa2-EDS20

-continued
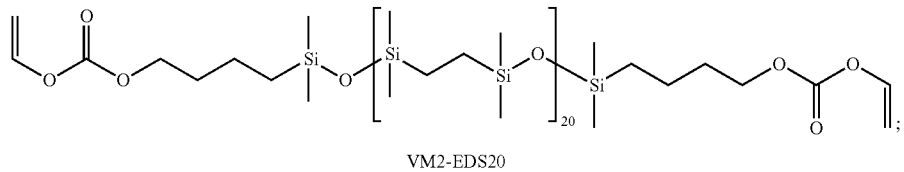
VM2-EDS20
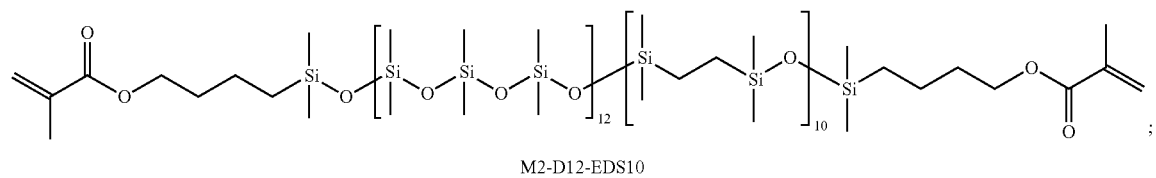
M2-D12-EDS10
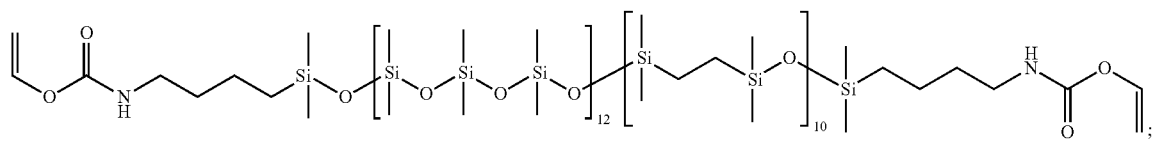
VMa2-D12-EDS10
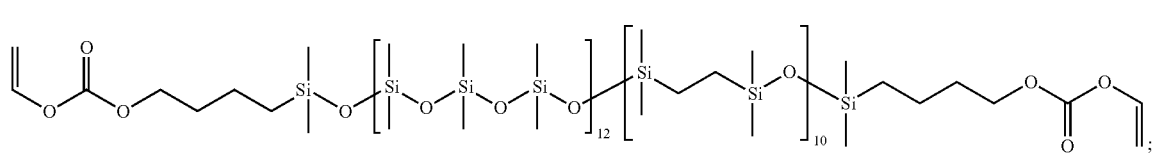
VM2-D12-EDS10
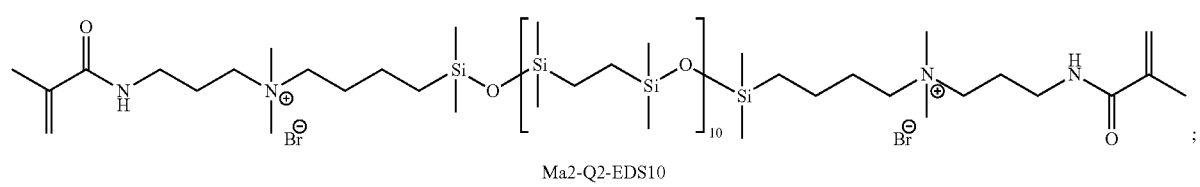
Ma2-Q2-EDS10
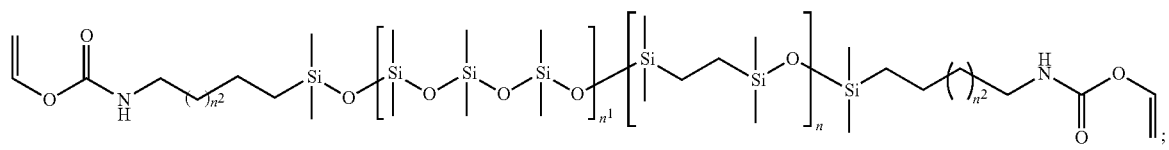
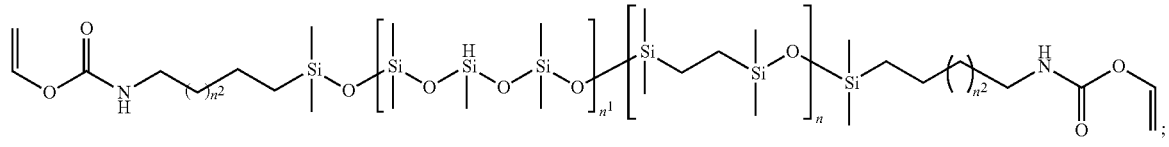

(XXVIII)
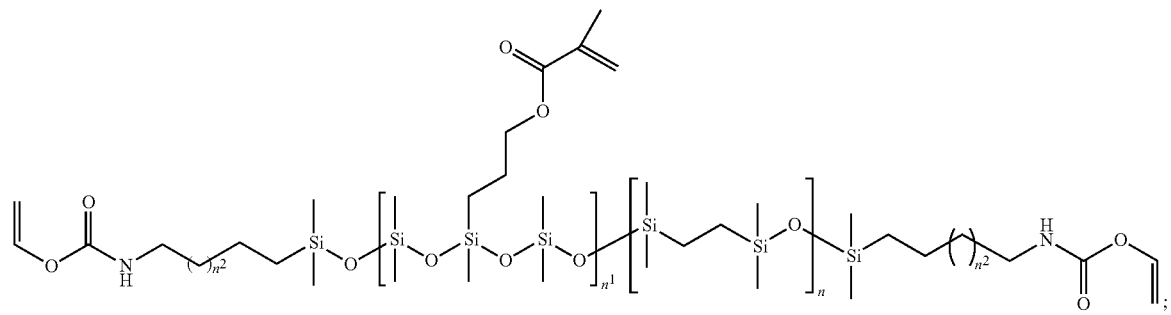
(XXIX)
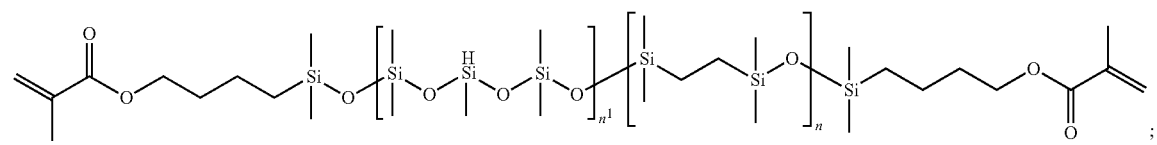
(XXX)
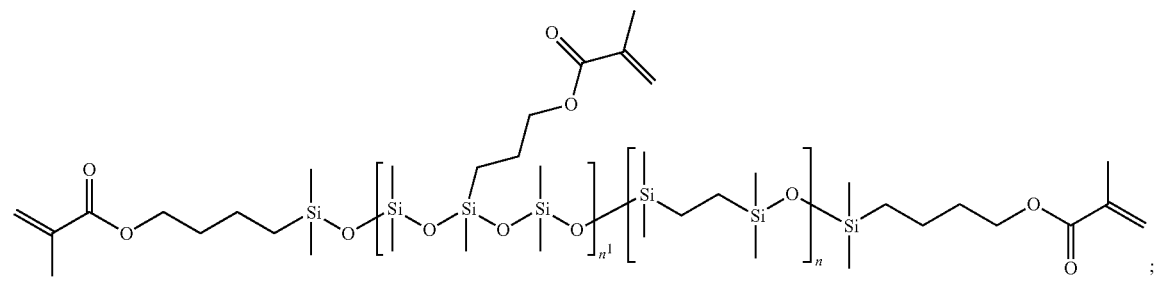
(XXXI)
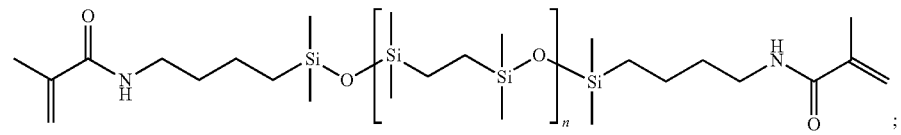
(XXXII)
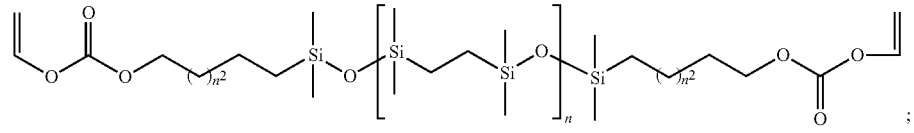
(XXXIII)
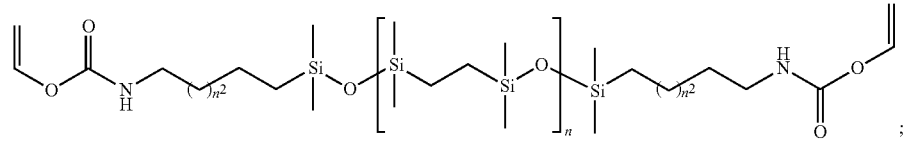
(XXXIV)
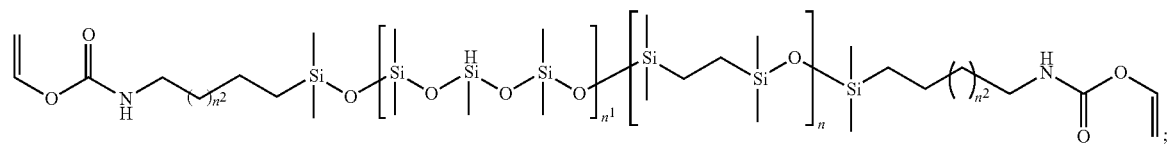

-continued

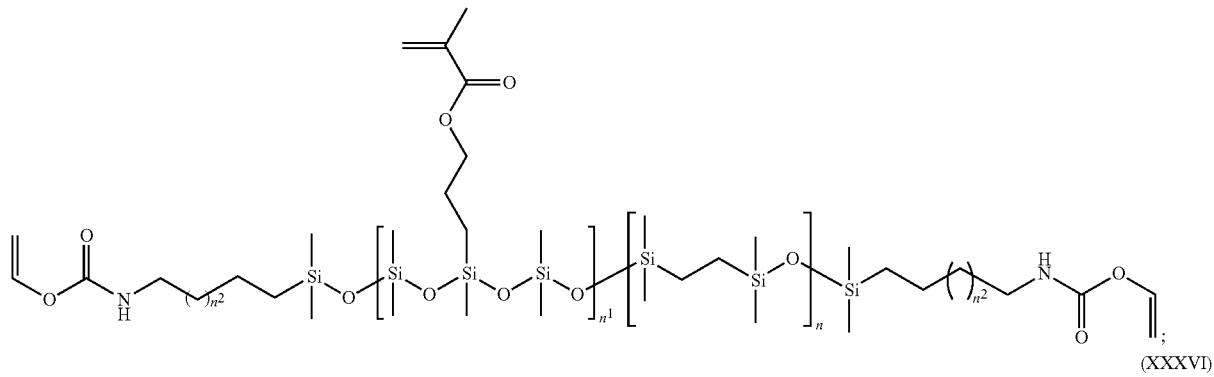
(XXXV)

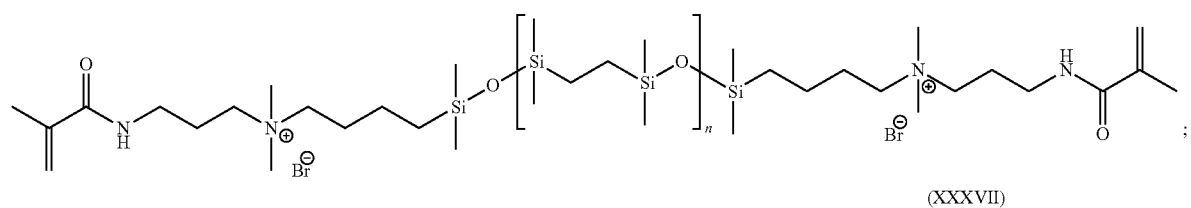
(XXXVI)

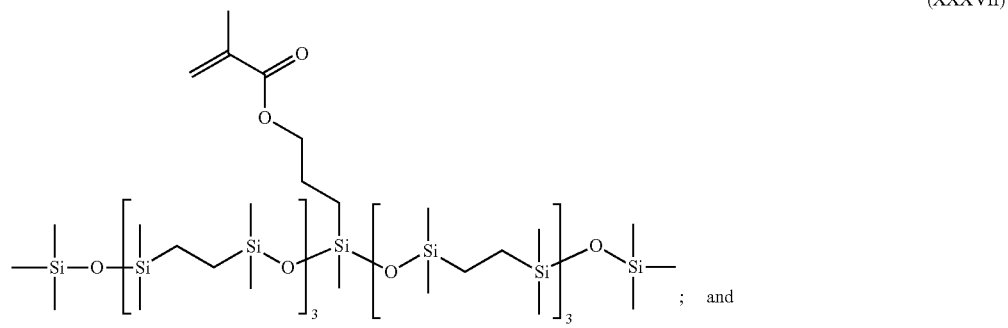
(XXXVII)

; and

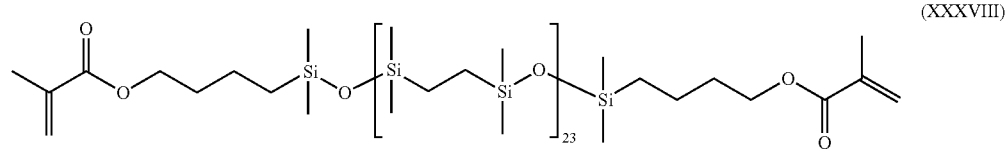
(XXXVIII)

Wherein for any one of formulae (XXVI)-(XXXVIII), when present n, $n^1$ and $n^2$ are as defined above.

7. A monomer mix comprising at least one monomer selected from the group consisting of the monomers of preferred embodiment 6.
8. The monomer mix of preferred embodiment 7 which when polymerized forms a medical device.
9. The monomer mix of preferred embodiment 7 further comprising a second copolymerizable monomer.
10. The monomer mix of preferred embodiment 9 further comprising a third copolymerizable monomer.
11. The monomer mix of preferred embodiment 8 wherein the medical device formed is selected from the group consisting of rigid contact lenses, soft contact lenses, phakic intraocular lenses, aphakic intraocular lenses and corneal implants.
12. The monomer mix of preferred embodiment 9 wherein the medical device formed is selected from the group consisting of rigid contact lenses, soft contact lenses, phakic intraocular lenses, aphakic intraocular lenses and corneal implants.
13. The monomer mix of preferred embodiment 8 wherein the medical device formed is selected from the group consisting of artificial heart valves, films, surgical devices, vessel substitutes, intrauterine devices, membranes, diaphragms, surgical implants, artificial blood vessels, artificial ureters, artificial breast tissue, membranes intended to come into contact with body fluid outside of the body, membranes for kidney dialysis machines, membranes for heart/lung machines, catheters, mouth guards, denture liners, ophthalmic devices, and hydrogel contact lenses.
14. The monomer mix of preferred embodiment 9 wherein the medical device formed is selected from the group consisting of artificial heart valves, films, surgical devices, vessel substitutes, intrauterine devices, membranes, diaphragms, surgical implants, artificial blood vessels, artificial ureters, artificial breast tissue, membranes intended to come into contact with body fluid outside of the body, membranes for kidney dialysis machines, membranes for heart/lung machines, catheters, mouth guards, denture liners, ophthalmic devices, and hydrogel contact lenses.
15. The monomer mix of preferred embodiment 14 wherein the medical device is a contact lens.

16. The monomer mix of preferred embodiment 15 wherein the medical device is a hydrogel contact lens.
17. The monomer mix of preferred embodiment 3 further comprising at least one mono ethylenically unsaturated free radical polymerizable group comprising polycarbosiloxane monomer.
18. The monomer mix of preferred embodiment 4 further comprising a mono ethylenically unsaturated free radical polymerizable group comprising polycarbosiloxane monomer.
19. The monomer mix of preferred embodiment 28 wherein the mono ethylenically unsaturated polymerizable group comprising polycarbosiloxane monomer is present in an amount from about 0.1 to about 30 percent by weight of the monomer mix.
20. The monomer mix of preferred embodiment 6 wherein the polycarbosiloxane monomer is present in an amount from about 0.1 to about 20 percent by weight of the monomer mix.
21. The monomer mix of preferred embodiment 6 wherein the polycarbosiloxane monomer is present in an amount from about 5 to about 15 percent by weight of the monomer mix.
22. The monomer mix of preferred embodiment 6 wherein the polycarbosiloxane monomer is present in an amount from about 0.1 to about 30 percent by weight of the monomer mix.
23. The monomer mix of preferred embodiment 6 wherein the mono ethylenically unsaturated polymerizable group comprising polycarbosiloxane monomer is present in an amount from about 0.1 to about 20 percent by weight of the monomer mix.
24. The monomer mix of preferred embodiment 9 wherein the polycarbosiloxane monomer is present in an amount from about 5 to about 15 percent by weight of the monomer mix.
25. The monomer mix of preferred embodiment 9 wherein the second copolymerizable monomer is a hydrophobic silicone comprising monomer.
26. The monomer mix of preferred embodiment 25 wherein the hydrophobic silicone comprising monomer is present in the monomer mix between about 0.1 to about 75.8 percent by weight.
27. The monomer mix of preferred embodiment 26 wherein the hydrophobic silicone comprising monomer is present in the monomer mix between about 2 to about 20 percent by weight.
28. The monomer mix of preferred embodiment 27 wherein the hydrophobic silicone comprising monomer is present in the monomer mix between about 5 to about 13 percent by weight.
29. The monomer mix of preferred embodiment 21 wherein the second copolymerizable second monomer is a hydrophilic monomer.
30. The monomer mix of preferred embodiment 29 wherein the hydrophilic monomer is present in the monomer mix between about 0.1 to about 75.8 percent by weight.
31. The monomer mix of preferred embodiment 30 wherein the hydrophilic monomer is present in the monomer mix between about 2 to about 20 percent by weight.
32. The monomer mix of preferred embodiment 30 wherein the hydrophilic monomer is present in the monomer mix between about 5 to about 13 percent by weight.
33. The monomer mix of preferred embodiment 29 further comprising a non-silicone comprising hydrophobic monomer.
34. The monomer mix of preferred embodiment 33 wherein the second copolymerizable monomer is a non-silicone comprising hydrophobic monomer.
35. The monomer mix of preferred embodiment 34 wherein the non-silicone comprising hydrophobic monomer is present at about 0 to about 60 percent by weight.
36. The monomer mix of preferred embodiment 33 wherein the non-silicone comprising hydrophobic monomer is selected from the group consisting of alkyl acrylates and alkyl methacrylates.
37. The monomer mix of preferred embodiment 25 wherein the second copolymerizable monomer is selected from the group consisting of methacryloxypropyl tris(trimethylsiloxy)silane ("TRIS"), pentamethyldisiloxy methylmethacrylate, tris(trimethylsiloxy)methacryloxy propylsilane, phenyltretramethyldisloxanylethyl acrylate, methyldi(trimethylsiloxy)methacryloxymethyl silane, 3-[tris(trimethylsiloxy)silyl]propyl vinyl carbamate, 3[tris(trimethylsiloxy)silyl] propyol allyl carbamate, and 3-[tris(trimethylsiloxy)silyl]propyl vinyl carbonate and mixtures thereof.
38. The monomer mix of preferred embodiment 21 wherein the bulky monomer is present at about 0 to about 41.2 percent by weight.
39. The monomer mix of preferred embodiment 38 wherein the bulky monomer is present at about 34 to about 41 percent by weight.
40. The monomer mix of preferred embodiment 21 wherein the bulky monomer is present at about 25 to about 41 percent by weight.
41. The monomer mix of preferred embodiment 25 wherein the monomer mix comprises a mixture comprising at least one silicone-comprising monomer and at least one hydrophilic monomer.
42. The monomer mix of preferred embodiment 41 wherein the monomer mix comprises a separate crosslinker.
43. The monomer mix of preferred embodiment 42 wherein the separate crosslinker is selected from the group consisting of methacrylates, ethylene glycol dimethacrylate (EGDMA) and allyl methacrylate (AMA).
44. The monomer mix of preferred embodiment 43 wherein the separate crosslinker is present at between about 0 to about 76 percent by weight.
45. The monomer mix of preferred embodiment 43 wherein the separate crosslinker is present at between about 2 to about 20 percent by weight.
46. The monomer mix of preferred embodiment 43 wherein the separate crosslinker is present at between about 5 to about 13 percent by weight.
47. The monomer mix of preferred embodiment 41 wherein the silicone-comprising monomer is a crosslinking agent.
48. The monomer mix of preferred embodiment 29 wherein the hydrophilic monomer is selected from the group consisting of unsaturated carboxylic acids, methacrylic acids, acrylic acids; acrylic substituted alcohols, 2-hydroxyethyl methacrylate, 2-hydroxyethyl acrylate; vinyl lactams, N-vinylpyrrolidone (NVP), 1-vinylazonan-2-one; acrylamides, methacrylamide, N,N-dimethylacrylamide (DMA) and mixtures thereof.
49. The monomer mix of preferred embodiment 48 wherein the hydrophilic monomer is present, separately or by combined weight in amounts of between about 0 to about 60 percent by weight.
50. The monomer mix of preferred embodiment 29 wherein the hydrophilic monomer is present, separately or by combined weight in amounts between about 20 to about 45 percent by weight.

51. The monomer mix of preferred embodiment 29 wherein the hydrophilic monomer is present, separately or by combined weight in amounts between about 0 to about 48.6 percent by weight.

52. The monomer mix of preferred embodiment 29 wherein the hydrophilic monomer is present, separately or by combined weight in amounts between about 0 to about 30 percent by weight.

53. The monomer mix of preferred embodiment 29 wherein the hydrophilic monomer is present, separately or by combined weight in amounts between about 0 to about 25 percent by weight.

54. The monomer mix of preferred embodiment 29 wherein the hydrophilic monomer is present, separately or by combined weight in amounts between about 0 to about 9.5 percent by weight.

55. The monomer mix of preferred embodiment 29 wherein the hydrophilic monomer is present, separately or by combined weight in amounts between about 2 to about 7 percent by weight.

56. The monomer mix of preferred embodiment 21 wherein the second copolymerizable monomer is a hydrophilic monomer.

57. The monomer mix of preferred embodiment 48 further comprising an organic diluent.

58. The monomer mix of preferred embodiment 57 wherein the organic diluent is selected from the group consisting of alcohols, tert-butanol (TBA), tert-amyl alcohol, hexanol and nonanol; diols, ethylene glycol; polyols, glycerol and mixtures thereof.

59. The monomer mix of preferred embodiment 58 wherein the organic diluent is present at about 0 to about 60% by weight of the monomeric mixture.

60. The monomer mix of preferred embodiment 58 wherein the organic diluent is present at about 1 to about 40% by weight.

61. The monomer mix of preferred embodiment 58 wherein the organic diluent is present at about 2 to about 30% by weight.

62. The monomer mix of preferred embodiment 58 wherein the organic diluent is present at about 3 to about 25% by weight.

63. The monomer mix of preferred embodiment 43 further comprising an organic diluent.

64. The monomer mix of preferred embodiment 63 wherein the organic diluent is selected from the group consisting of alcohols, tert-butanol (TBA), tert-amyl alcohol, hexanol and nonanol; diols, ethylene glycol; polyols, glycerol and mixtures thereof.

65. The monomer mix of preferred embodiment 64 wherein the organic diluent is present at about 0 to about 60% by weight of the monomeric mixture.

66. The monomer mix of preferred embodiment 64 wherein the organic diluent is present at about 1 to about 40% by weight.

67. The monomer mix of preferred embodiment 66 wherein the organic diluent is present at about 2 to about 30% by weight.

68. The monomer mix of preferred embodiment 66 wherein the organic diluent is present at about 3 to about 25% by weight.

69. A hydrogel contact lens comprising a polymerized monomer mix comprising a polymerizable monomer mixture comprising about 0.1 to about 75.8 percent by weight of a methacrylamide crosslinker, about 0 to about 41.2 percent by weight of a bulky siloxane monomer, about 0 to about 78 percent by weight of at least one hydrophilic monomer, about 0 to about 48.6 percent by weight of an alcohol, about 0.1 to about 29.9 weight percent of a polycarbosiloxane monomer, about 0.1 to about 1.0 percent by weight of an initiator and about 90 to about 200 parts per million of a visibility tint.

70. The hydrogel contact lens of preferred embodiment 69 comprising as part of polymerizable monomer mixture comprising about 5 to about 13 percent by weight of a methacrylamide crosslinker, about 34 to about 41 percent by weight of a bulky siloxane monomer, about 28 to about 52 percent by weight of at least one hydrophilic monomer, about 0 to about 25 percent by weight of an alcohol, about 5 to about 15 weight percent of polycarbosiloxane monomer, about 0.2 to about 0.8 percent by weight of an initiator and about 90 to about 145 parts per million of a visibility tint.

71. The hydrogel contact lens of preferred embodiment 69 comprising as part of the polymerizable monomer mixture comprising about 2 to about 8 percent by weight of a methacrylamide crosslinker, about 25 to about 38 percent by weight of a bulky siloxane monomer, about 35 to about 45 percent by weight of at least one hydrophilic monomer, about 3 to about 8 percent by weight of an alcohol, about 10 to about 13 weight percent of a polycarbosiloxane monomer, about 0.3 to about 0.6 percent by weight of an initiator and about 145 to about 200 parts per million of a visibility tint.

72. A monomer mix useful for forming a medical device wherein the monomer mix comprises at least one monomer selected from the group consisting of any one of the monomers of preferred embodiments 6 and when polymerized forms an ophthalmic medical device to be implanted in or on an eye.

73. A medical device comprising a polymerized monomer mix comprising any one of the monomer of embodiment 6.

It will be understood that various modifications may be made to the embodiments disclosed herein. Therefore the above description should not be construed as limiting, but merely as exemplifications of preferred embodiments. For example, the functions described above and implemented as the best mode for operating the present application are for illustration purposes only. Other arrangements and methods may be implemented by those skilled in the art without departing from the scope and spirit of this application. Moreover, those skilled in the art will envision other modifications within the scope and spirit of the features and advantages appended hereto.

What is claimed is:

1. An article of manufacture selected from the group consisting of contact lenses, phakic and aphakic intraocular lenses and corneal implants; wherein the article is formed from polymerizing a monomer mixture including an ethylenically unsaturated free radical polymerizable polycarbosiloxane monomer of formula (I) and at least a second free radical copolymerizable monomer, wherein the polycarbosiloxane monomer of formula (I) is present at from about 0.1 to about 30 percent by weight of the monomer mixture:

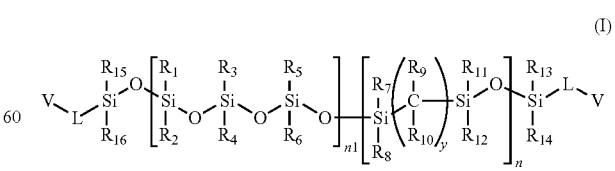

(I)

wherein $R_1, R_2, R_4, R_5, R_6, R_7, R_8, R_{11}, R_{12}, R_{13}, R_{14}, R_{15}$ and $R_{16}$ are each independently a monovalent atom or group selected from H, alkyl, halo alkyl, heteroalkyl, cyclo alkyl, heterocyclo alkyl, alkenyl, halo alkenyl, or aromatic; wherein $R_3$ is a monovalent atom or group selected from H, alkyl, halo alkyl, heteroalkyl, cyclo alkyl, heterocyclo alkyl, alkenyl, halo alkenyl, aromatic or methacryloxypropyl; wherein at least one of $R_9$ or $R_{10}$ is hydrogen, and the other of $R_9$ and $R_{10}$ may not be present when monomers of formula (I) comprise -[silyl-alkenyl-siloxy]- units, and when present in a monomer comprising -[silyl-alkyl-siloxy]- units is independently a monovalent atom or group selected from H, alkyl, alkene, alkyne; y is 2-7; n is 1-100; $n_1$ is greater than zero and up to 10; L is the same or different and is a divalent linker group or a bond; and V is an ethylenically unsaturated free radical polymerizable monovalent group.

2. An article of manufacture of claim 1, wherein y is 2.
3. An article of manufacture of claim 2, wherein n is 2-80.
4. An article of manufacture of claim 2, wherein n is 3-20.
5. An article of manufacture of claim 2, wherein n is 5-15.
6. The article of manufacture of claim 1 wherein the article is a contact lens.
7. The article of manufacture of claim 6 wherein the article is a hydrogel contact lens.
8. The article of manufacture of claim 1 and the monomer mixture comprises at least second and third copolymerizable monomers.
9. The article of manufacture of claim 8, wherein the monomer mixture comprises from 0.1 to 75.8 percent by weight of a second copolymerizable silicone comprising hydrophobic monomer, 0 to 60 percent by weight of non-silicone comprising hydrophobic monomers, and 0.1 to 75.8 percent by weight of hydrophilic monomers.

10. The article of manufacture of claim 9 wherein the monomer mixture comprises a bulky monomer selected from the group consisting of methacryloxypropyl tris(trimethylsiloxy)silane ("TRIS"), pentamethyldisiloxy methylmethacrylate, tris(trimethylsiloxy) methacryloxy propylsilane, phenyltretramethyl-disloxanylethyl acrylate, methyldi (trimethylsiloxy) methacryloxymethyl silane, 3-[tris (trimethylsiloxy)silyl]propyl vinyl carbamate, 3-[tris (trimethylsiloxy)silyl]propyol allyl carbamate, and 3-[tris (trimethylsiloxy)silyl]propyl vinyl carbonate and mixtures thereof.

11. The article of manufacture of claim 10 wherein the bulky monomer is present at about 25 to about 41 percent by weight of the monomer mixture.

12. An article of manufacture of claim 1, wherein the polycarbosiloxane monomer is of formula (III), (XXVI), (XXVII), (XXVIII), (XXIX), (XXX), (XXXIV), or (XXXV):

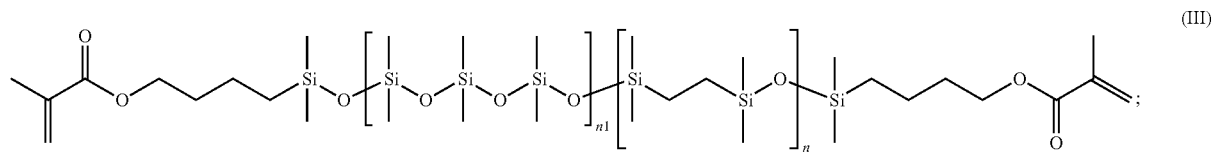

(III)

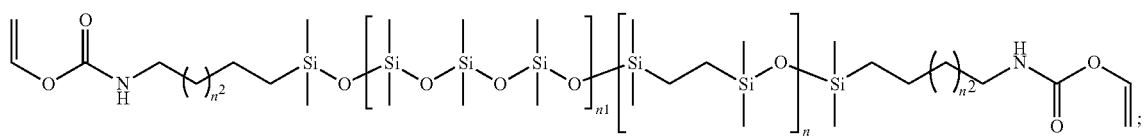

(XXVI)

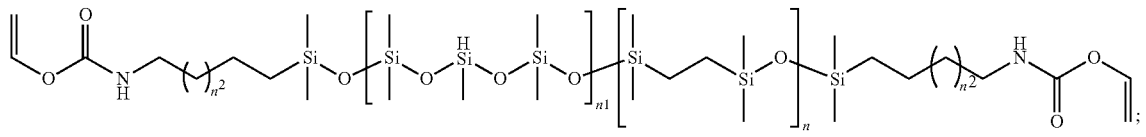

(XXVII)

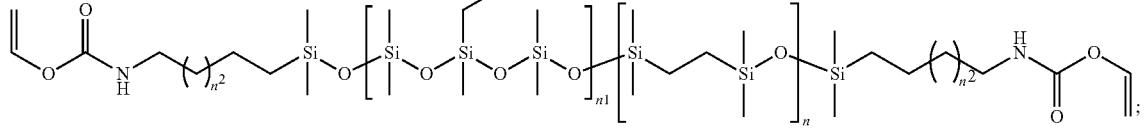

(XXVIII)

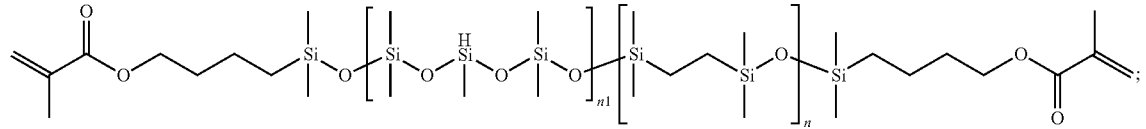

(XXIX)

(XXX)
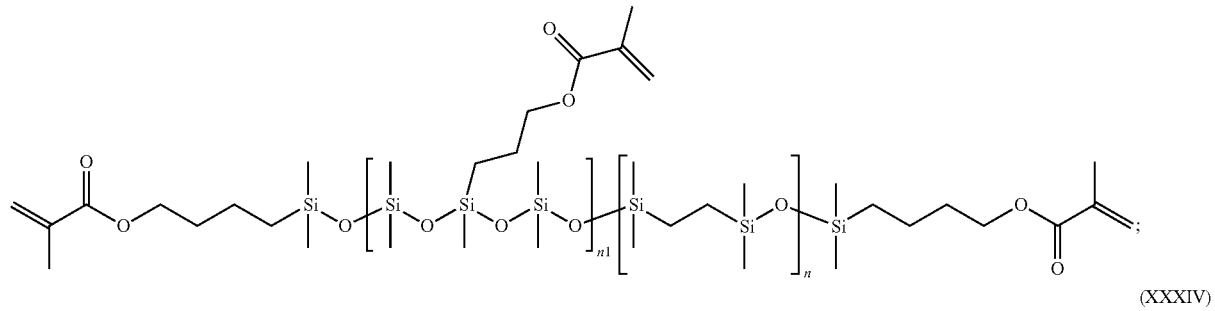
(XXXIV)
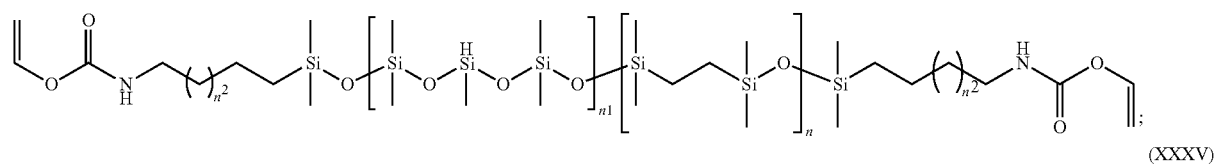
(XXXV)
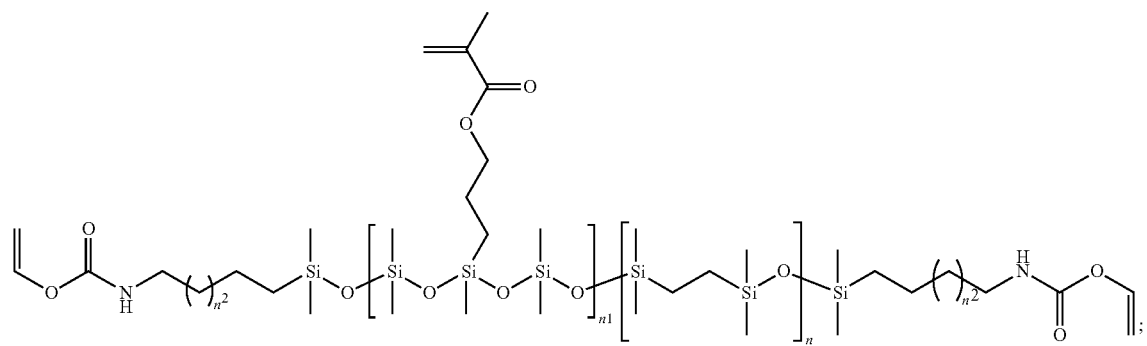
wherein $n^2$ is 0 to 10.
13. An article of manufacture of claim 1, wherein the polycarbosiloxane monomer is of formula (III):
(III)
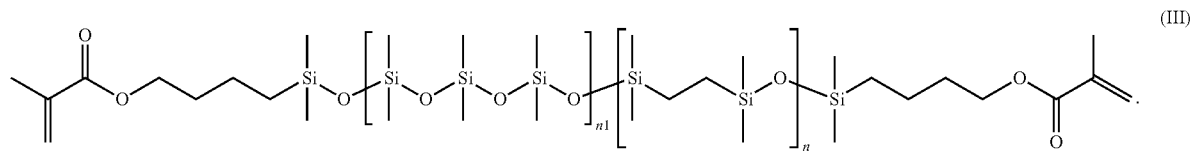
14. An article of manufacture of claim 1, wherein the polycarbosiloxane monomer is of formula (XXVI), (XXVII) or (XXVIII):
(XXVI)
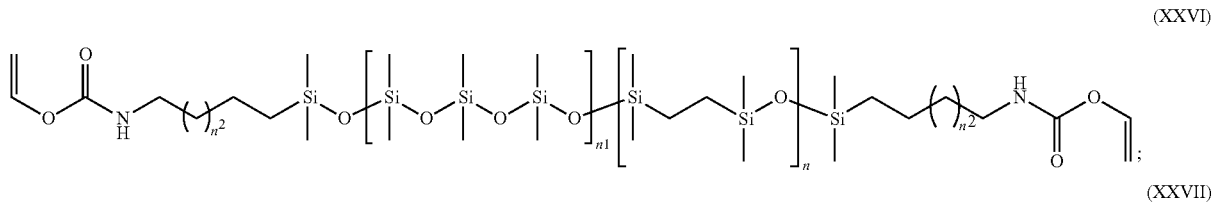
(XXVII)
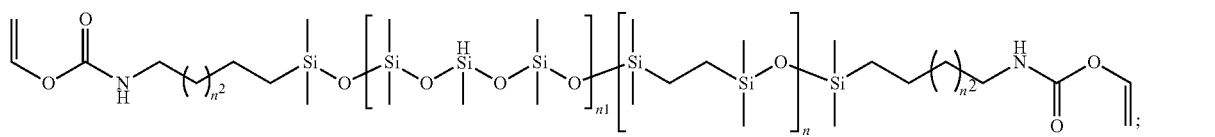

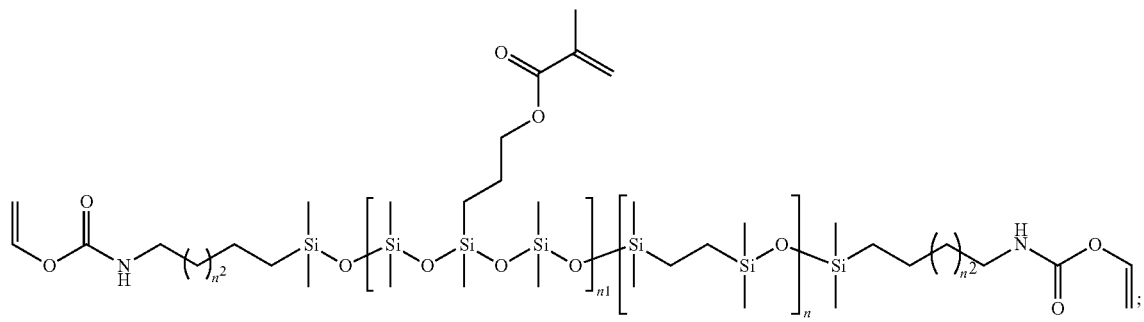
(XXVIII)
wherein $n^2$ is 0 to 10.
15. An article of manufacture of claim 1, wherein the polycarbosiloxane monomer is of formula (XXIX) or (XXX):
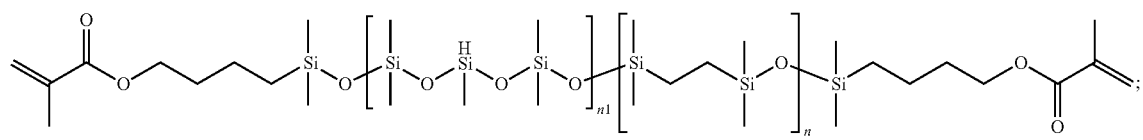
(XXIX)
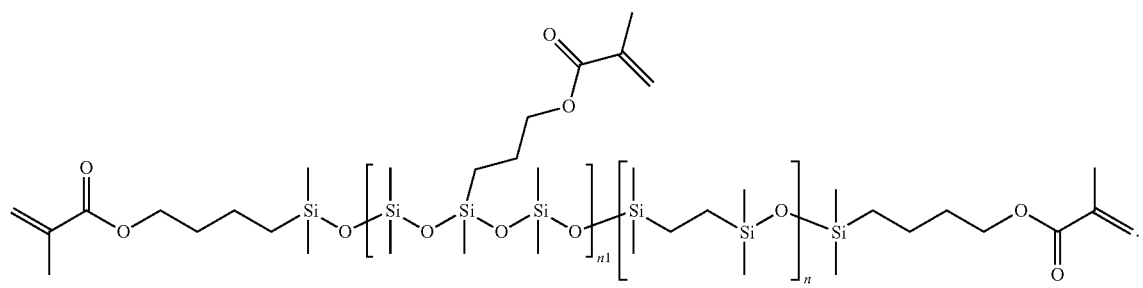
(XXX)
16. An article of manufacture of claim 1, wherein the polycarbosiloxane monomer is of formula (XXXIV) or (XXXV):
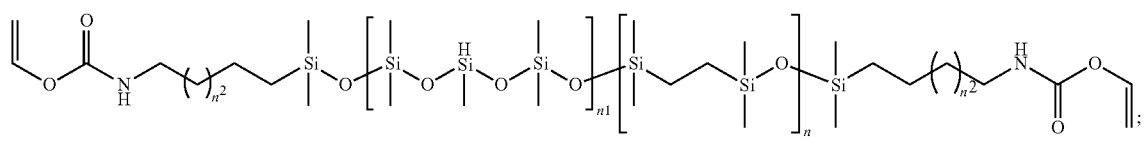
(XXXIV)
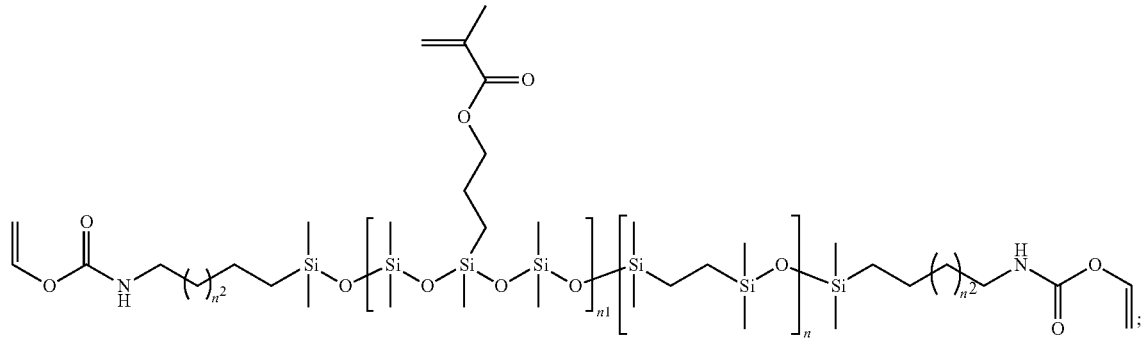
(XXXV)
wherein $n^2$ is 0 to 10.

17. An article of manufacture of claim 1, wherein the polycarbosiloxane monomer is of formula (IX):
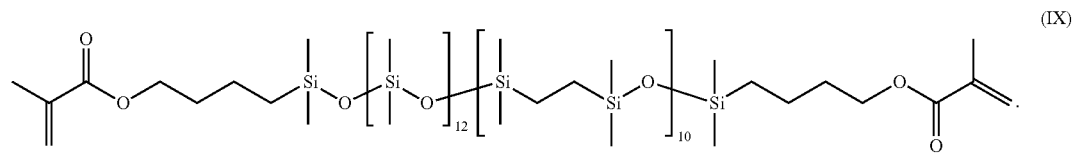
18. An article of manufacture of claim 1, wherein n is 2-80.
19. An article of manufacture of claim 1, wherein n is 3-20.
20. An article of manufacture of claim 1, wherein n is 5-15.
* * * * *